US009593341B2

(12) United States Patent
Bodie et al.

(10) Patent No.: US 9,593,341 B2
(45) Date of Patent: *Mar. 14, 2017

(54) FILAMENTOUS FUNGI HAVING AN ALTERED VISCOSITY PHENOTYPE

(75) Inventors: Elizabeth A. Bodie, San Carlos, CA (US); Robert James Pratt, II, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 139 days.

This patent is subject to a terminal disclaimer.

(21) Appl. No.: 14/113,799

(22) PCT Filed: Apr. 20, 2012

(86) PCT No.: PCT/US2012/034409
§ 371 (c)(1),
(2), (4) Date: Jun. 13, 2014

(87) PCT Pub. No.: WO2012/145598
PCT Pub. Date: Oct. 26, 2012

(65) Prior Publication Data

US 2014/0315313 A1 Oct. 23, 2014

Related U.S. Application Data

(60) Provisional application No. 61/478,160, filed on Apr. 22, 2011, provisional application No. 61/478,162, filed on Apr. 22, 2011, provisional application No. 61/480,602, filed on Apr. 29, 2011, provisional application No. 61/480,610, filed on Apr. 29, 2011, provisional application No. 61/480,629, filed on Apr. 29, 2011.

(51) Int. Cl.
| | |
|---|---|
| *C12N 1/00* | (2006.01) |
| *C12N 15/79* | (2006.01) |
| *C12N 1/14* | (2006.01) |
| *C12N 15/80* | (2006.01) |
| *C12N 1/36* | (2006.01) |
| *C12N 9/24* | (2006.01) |

(52) U.S. Cl.
CPC .............. *C12N 15/79* (2013.01); *C12N 1/14* (2013.01); *C12N 1/36* (2013.01); *C12N 9/2405* (2013.01); *C12N 15/80* (2013.01)

(58) Field of Classification Search
CPC ..................................................... C12N 15/79
See application file for complete search history.

(56) References Cited

U.S. PATENT DOCUMENTS 7,371,581 B2 * 5/2008 Gunnewijk ............ G01N 33/68
435/288.4

FOREIGN PATENT DOCUMENTS

| WO | WO 01/09352 | 2/2001 |
|---|---|---|
| WO | WO 2005/001036 | 1/2005 |
| WO | WO 2012/027580 | 3/2012 |
| WO | WO 2012/145584 | 10/2012 |
| WO | WO 2012/145592 | 10/2012 |
| WO | WO 2012/145595 | 10/2012 |
| WO | WO 2012/145596 | 10/2012 |

OTHER PUBLICATIONS

Borgia et al (Molecular Microbiology vol. 20, No. 6, pp. 1287-1296, 1996).*
Altschul, et al., "basic local alignment search tool," (1990) *J. Mol. Biol.*, 215:403-10.
Altschul, et al., "local alignment statistics," (1996) *Meth. Enzymol.*, 266:460-80.
Borgia, et al., "The ORLA gene from aspergillus nidulans encodes a trehalose-6-phosphate phosphatase necessary for normal growth and chitin synthesis at elevated temperatures," (1996) *Molecular Biology*, vol. 20, No. 6, pp. 1287-1296.
Dai, et al., "Identification of genes associated with morphology in aspergillus niger by using suppression subtractive hybridization," (2004) *Applied and Environmental Microbiology*, vol. 70, No. 4, pp. 2474-2485.
Devereux, et al., "A comprehensive set of sequence analysis programs for the VAX," (1984) *Nucleic Acids Res.*, 12:387-95.
Feng and Doolittle, "Progressive Sequence Alignment as a Prerequisite to Correct Phylogenetic Trees," (1987) *J. Mol. Evol.*, 35:351-60.
Gancedo, et al., "The importance of a functional trehalose biosynthetic pathway for the life of yeasts and fungi," (2004) *FEMS Yeast Research*, vol. 4, No. 4-5, pp. 351-359.
Garcia, et al., "The Global Transcriptional Response to Transient Cell Wall Damage in *Saccharomyces cerevisiae* and Its Regulation by the Cell Integrity Signaling Pathway," (2004) *J. Biol. Chem.*, 279:15183-15195.
Henikoff and Henikoff, "Amino acid substitution matrices from protein blocks," (1989) *Proc. Natl. Acad. Sci.*, USA, 89:10915-10919.
Higgins, et al., "CLUSTAL: a package for performing multiple sequence alignment on a microcomputer," (1988) *Gene*, 73:237-244.
Higgins and Sharp, "Fast and sensitive multiple sequence alignments on a microcomputer," (1989), *CABIOS*, 5:151-53.
Hughes, et al., "Assembly, organization, and function of the COPII coat," (2008) *Histochem Cell Biol.*, 129: pp. 129-151.
International Search Report and the Written Opinion of the International Searching Authority for International Application No. PCT/US2012/034409, mailed Aug. 14, 2012.

(Continued)

*Primary Examiner* — Albert Navarro
(74) *Attorney, Agent, or Firm* — Danisco US Inc.

(57) ABSTRACT

Described are compositions and methods relating to variant filamentous fungi having altered growth characteristics. Such variants are well-suited for growth in submerged cultures, e.g., for the large-scale production of enzymes and other proteins for commercial applications.

37 Claims, 1 Drawing Sheet

(56) References Cited

OTHER PUBLICATIONS

Karababa, et al., "CRZ1, a target of the calcineurin pathway in *Candida albicans*," *Molecular Microbiology*, (2006) 59(5), 1429-1451.
Karhinen, et al., "Endoplasmic reticulum exit of a secretory Glycoprotein in the absence of Sec24p family proteins in yeast," (2005) *Traffic*, 6: pp. 562-574.
Karlin, et al., "Applications and statistics for multiple high scoring segments in molecular sequences," (1993) *Proc. Natl. Acad. Sci.*, USA, 90:5873-87.
Kothe, G. and Free, S., "Calcineurin Subunit B Is Required for Normal Vegetative Growth in Neurospora *crassa*," (1998) *Fungal Genetics and Biology*, 23, 248-258.
Munro, et al., "Cellular Symmetry Breaking during Caenorhabditis *elegans* Development," (2009) *Cold Spring Herb Perspect Biol.*, pp. 1-20.
Needleman and Wunsch, "A General Method Applicable to the Search for Similarities in the Amino Add Sequence of Two Proteins," (1970) *J. Mol. Biol.*, 48:443-453.
Pardini, et al., "The CRH Family Coding for Cell Wall Glycosylphosphatidylinositol Proteins with a Predicted Transglycosidase Domain Affects Cell Wall Organization and Virulence of *Candida albicans*," (2006) *J. Biol. Chem.*, 281:40399-4001.
Passolunghi, et al., "Cloning of the Zygosaccharomyces bailii GAS1 homologue and effect of cell wall engineering on protein secretory phenotype," (2010) *Microbial Cell Factories*, 9: 7, pp. 1-11.
Pearson and Lipman, "Improved tools for biological sequence comparison," (1988) *Proc. Natl. Acad. Sci.* USA 85:2444-2448.
Peng, et al., "Evidence for overlapping and distinct functions in protein transport of coat protein Sec24p family members," (2000) *The Journal of Biological Chemistry*, vol. 275, No. 15, pp. 11521-11528.

Peterbauer, et al., "The *Trichodenna atroviride* seb1 (stress response element binding) gene encodes an AGGGG-binding protein which is involved in the response to high osmolarity stress," (2002) *Molecular Genetics and Genomics*, 268:223-231.
Prokisch, et al., "Impairment of calcineurin function in *Neurospora crassa* reveals its essential role in hyphal growth, morphology and maintenance of the apical $Ca^{2+}$ gradient," (1997) *Mol Gen Genet*, 256: 104-114.
Roberg, et al., "LST1 is a SEC24 homologue used for selective export of the plasma membrane ATPase from the endoplasmic reticulum", (1999) *The Journal of Cell Biology*, vol. 145, No. 4, pp. 659-672.
Schirawski, et al., "Endoplasmic Reticulum Glucosidase II Is Required for Pathogenicity of Ustilago maydis," (2005) *The Plant Cell*, vol. 17, 3532-3543.
Shimoni, et al., "Lst1p and Sec24p cooperate in sorting of the plasma membrane ATPase into COPII vesicles in *Saccharomyces cerevisiae*," (1999) *The Journal of Cell Biology*, vol. 151, No. 5, pp. 973-984.
Simola, et al., "Trehalose is required for conformational repair of heat-denatured proteins in the yeast endoplasmic reticulum but not for maintenance of membrane traffic functions after severe heat stress," (2000) *Molecular Microbiology*, 37(1), pp. 42-53.
Singer, et al., "multiple effects of trehalose on protein folding in vitro and in vivo," (1998) *Molecular Cell*, vol. 1, pp. 639-648.
Smith and Waterman, "Comparison of Biosequences," (1981) *Adv. Appl. Math.*, 2:482-489.
Turchini, et al., "Increase of external osmolarity reduces morphogenetic defects and accumulation of Chitin in a gas1 mutant of *Saccharomyces cerevisiae*," (2000) *Journal of Bacteriology*, vol. 182, No. 4, pp. 1167-1171.
Yamazaki, et al., "A chitinase gene, chiB, involved in the autolytic process of Aspergillus nidulans," (2006) *Current Genetics*, vol. 51, No. 2, pp. 89-98.
Yoshimoto, et al., "Genome-wide Analysis of Gene Expression Regulated by the Calcineurin/Crzlp Signaling Pathway in Saccharo•yces cerevisilu," (2002) *J. Bio. Chem.*, 277:31079-31088.

* cited by examiner

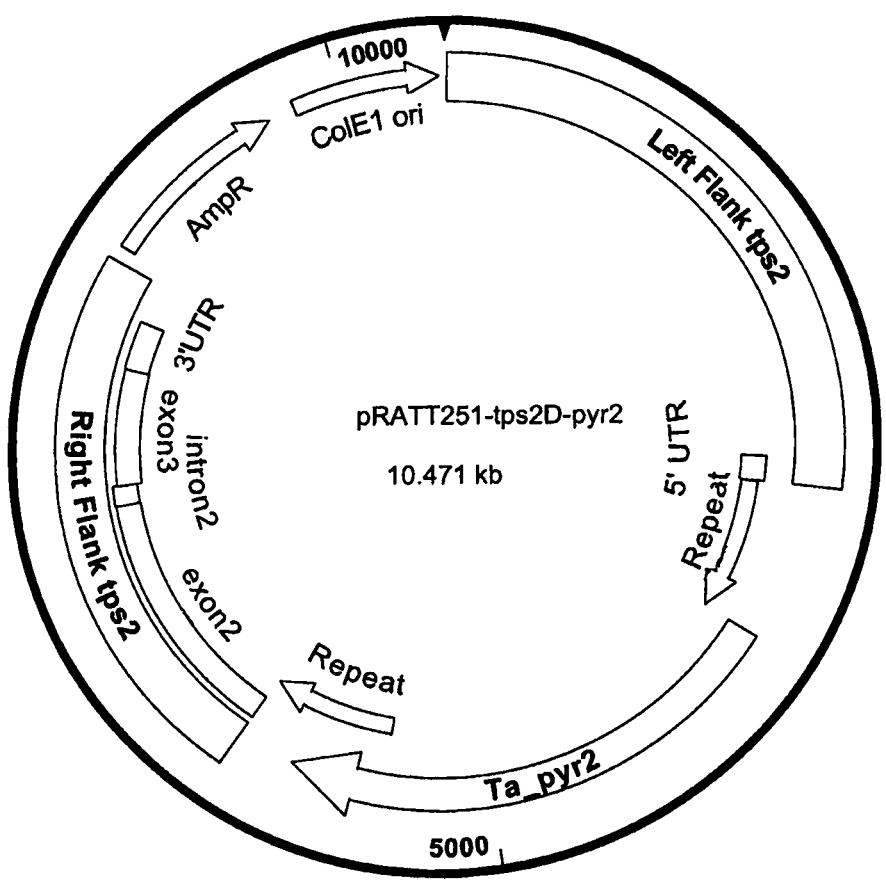

SEQUENCE LISTING

<160> NUMBER OF SEQ ID NOS: 14

<210> SEQ ID NO 1
<211> LENGTH: 874
<212> TYPE: PRT
<213> ORGANISM: Trichoderma reesei

<400> SEQUENCE: 1

Met Ala Arg Arg Glu Ser Leu Ser Glu Ile Arg Ala Ala Asn Pro Glu
1               5                   10                  15

Leu Phe Leu Thr Gly Asn Ile Ile Ser Ala Thr Phe Asn Ile Pro His
            20                  25                  30

Ala Val Thr Tyr His Lys Gly Gly Ala Trp Asp Leu Lys Pro Arg Arg
        35                  40                  45

Gly Gln Ser Ala Leu Ile Asp Ser Phe Ala Tyr Leu Ser Ser Asp Ala
    50                  55                  60

Thr Pro Trp Asn His Thr Val Val Ala Trp Thr Gly Glu Ile Ala Asn
65                  70                  75                  80

Pro Asp Asn Asp Pro Leu Ser Pro Pro Asp Thr Pro Ser Ala Ala Ala
                85                  90                  95

Thr Thr Ile Gly Ala Ala Asn Ser Leu Ser Ala Pro Val Pro Ile Asp
            100                 105                 110

Ala Thr Thr Arg Leu Pro Thr Pro Pro Val Asp Gly Leu Trp Ile
        115                 120                 125

Pro Lys Ala Asp Gln Thr Arg Leu Glu His Gln Leu Ser His Ser Thr
    130                 135                 140

Thr Ile Arg Thr Val Pro Val Trp Leu Ala Asp Gln Ser Glu Ala Thr
145                 150                 155                 160

-continued

Asp Asp Gly Ile Met Leu Lys Asp Gln Ala Arg Trp Arg Arg Tyr Ala
            165                 170                 175

Glu His Asp Leu Tyr Thr Leu Phe His Tyr Lys Gln His Glu Pro Thr
        180                 185                 190

Asp Gly Arg Lys Glu Arg Ala Gln Trp Ala Asp Tyr Arg Met Asn
        195                 200                 205

Gln Lys Phe Ala Asn Lys Ile Ile Glu Ile Tyr Lys Pro Gly Asp Val
    210                 215                 220

Val Ile Val His Asp Tyr Tyr Leu Met Leu Pro Ser Met Leu Arg
225                 230                 235                 240

Gln Arg Ala Pro Lys Met Tyr Ile Ser Phe Phe Leu His Ser Pro Phe
            245                 250                 255

Pro Ser Ser Glu Phe Leu Arg Cys Leu Pro Arg Arg Lys Glu Val Leu
            260                 265                 270

Glu Gly Val Leu Gly Ala Asn Leu Val Gly Phe Gln Ser Tyr Ser Tyr
        275                 280                 285

Ser Arg His Phe Leu Ser Cys Cys Thr Arg Ile Leu Gly Phe Pro Ser
    290                 295                 300

Asp Thr Leu Gly Ile Asp Ala Tyr Gly Ser Arg Val Gln Val Gly Val
305                 310                 315                 320

Phe Pro Ile Gly Ile Asp Ala Ala Lys Val Glu Thr Ala Ala Trp Ala
            325                 330                 335

Asp Thr Val Asn Glu Lys His Ala Ala Val Leu Lys Met Tyr Glu Gly
            340                 345                 350

Lys Lys Ile Ile Val Gly Arg Asp Arg Leu Asp Ser Val Arg Gly Val
        355                 360                 365

Ala Gln Lys Leu Gln Ala Phe Glu Arg Phe Leu Glu Leu Tyr Pro His
    370                 375                 380

Trp Arg Glu Lys Val Val Leu Ile Gln Val Thr Ser Pro Thr Ser Ile
385                 390                 395                 400

Glu Ala Glu Lys Gly Asp Pro Glu Asn Lys Asn Ala Ser Arg Val Asn
            405                 410                 415

Glu Leu Ile Thr Lys Ile Asn Gly Glu Tyr Gly Ser Leu Gly Phe Ser
            420                 425                 430

Pro Val Gln His Tyr Pro Gln Tyr Leu Ser Gln Ala Glu Tyr Phe Ala
        435                 440                 445

Leu Leu Arg Ala Ala Asp Ile Gly Leu Ile Thr Ser Val Arg Asp Gly
    450                 455                 460

Met Asn Thr Thr Ser Leu Glu Tyr Val Val Cys Gln Lys Asp Ser Asn
465                 470                 475                 480

Gly Pro Leu Ile Leu Ser Glu Phe Ser Gly Thr Ala Gly Ser Leu Arg
            485                 490                 495

Asp Ala Ile His Ile Asn Pro Trp Asp Leu Thr Gly Val Ala Glu Lys
        500                 505                 510

Ile Asn Ala Ala Leu Glu Met Ser Glu Glu Arg Val Lys Met Gln
    515                 520                 525

Thr Ser Leu Tyr Thr His Val Thr Thr Gln Asn Val Gln Ser Trp Ile
    530                 535                 540

Thr Lys Phe Ile Arg Lys Phe His Ala Ala Leu Ser Glu Thr Asn Ser
545                 550                 555                 560

Val Thr Ser Thr Pro Leu Leu Asp Arg Ala Leu Leu Leu Ser Arg Tyr
            565                 570                 575

Arg Ala Ala Lys Lys Arg Leu Phe Met Phe Asp Tyr Asp Gly Thr Leu

```
            580                 585                 590

Thr Pro Ile Val Arg Glu Pro Ser Ala Ala Val Pro Ser Glu Arg Ile
        595                 600                 605

Ile Arg Tyr Leu Gln Ser Leu Ala Ser Asp Pro Arg Asn Ala Val Trp
    610                 615                 620

Ile Ile Ser Gly Arg Asp Gln Glu Phe Leu Gln Gln His Leu Gly His
625                 630                 635                 640

Ile Pro Arg Ile Gly Phe Ser Ala Glu His Gly Ser Phe Met Arg Asp
                645                 650                 655

Pro Gly Ser Asp Glu Trp Val Asn Leu Ala Glu Lys Phe Asp Met Gly
            660                 665                 670

Trp Gln Ala Glu Val Met Glu Val Phe Gln Arg Tyr Thr Asp Lys Val
        675                 680                 685

Pro Gly Ser Phe Ile Glu Arg Lys Arg Cys Ala Leu Thr Trp His Tyr
    690                 695                 700

Arg Leu Ala Glu Pro Glu Gln Gly Leu His Met Ser Arg Glu Cys His
705                 710                 715                 720

Arg Glu Leu Glu Thr Gly Ile Ala Gln Arg Trp Glu Val Glu Val Met
                725                 730                 735

Pro Gly Lys Ala Asn Ile Glu Val Arg Pro Thr Phe Ile Asn Lys Gly
            740                 745                 750

Glu Ile Ala Lys Arg Leu Val Ala Thr Tyr His Asn Pro Gly Ala Ala
        755                 760                 765

Pro Thr Asp Lys Asp Pro Tyr Pro Gly Lys Ile Glu Phe Ala Leu Cys
    770                 775                 780

Ser Gly Asp Asp Phe Thr Asp Glu Asp Met Phe Arg Ser Leu Asn Gly
785                 790                 795                 800

Ala Cys Gly Thr Ile Leu Glu Asp Gln His Val Phe Thr Val Thr Val
                805                 810                 815

Gly Ala Ser Thr Lys Val Thr Leu Ala Lys Trp His Leu Leu Glu Pro
            820                 825                 830

Glu Asp Val Ile Glu Cys Val Gly Leu Leu Ala Gly Ala Gly Asp Pro
        835                 840                 845

Ala Ser Leu Glu Arg Val Gly Glu Val Asn Leu Ala Ala Leu Ser Gln
    850                 855                 860

Val Glu Gly His Ile Pro Ala Glu Glu Leu
865                 870

<210> SEQ ID NO 2
<211> LENGTH: 872
<212> TYPE: PRT
<213> ORGANISM: Beauveria bassiana

<400> SEQUENCE: 2

Met Ala Arg Arg Glu Ser Leu Ser Glu Ile Leu Ala Ala Asn Pro Glu
1               5                   10                  15

Leu Ser Leu Ser Gly Ser Ile Ile Ser Ala Ala Phe Asn Ile Pro His
            20                  25                  30

Ala Leu Thr Tyr Arg Lys Gly Gly Asp Trp Gly Leu Lys Pro Arg Gly
        35                  40                  45

Gly Gln Ser Ala Leu Phe Asp Ser Phe Ala Tyr Leu Ser Ser Ser Ala
    50                  55                  60

Asn Pro Phe Lys His Thr Val Val Ser Trp Thr Gly Glu Ile Asp Ser
65                  70                  75                  80
```

```
Pro Gln Gly Pro Leu Glu Pro Glu Pro Gln Arg Pro Arg Ser Thr Thr
            85                  90                  95

Val Gly Val Ser Ser Leu Asn Pro Leu Ser Ala Pro Ile Pro Val Asp
100                 105                 110

Gly Ile Val Gln Leu Pro Thr Pro Pro Ser Ser Asp Gly Leu Trp Leu
            115                 120                 125

Pro Lys Ala Asp Gln Glu Arg Leu Glu His Gln Leu Ser Asn Asp Lys
130                 135                 140

Thr Ile Arg Thr Val Pro Val Trp Leu Ala Glu Asp Glu Ile Thr
145                 150                 155                 160

Pro Asp Gly Ile Met Leu Arg Asp Gln Gly Arg Trp Arg Gly Tyr Ala
                165                 170                 175

His Arg Asp Leu Tyr Ser Leu Phe His Tyr Lys Gln His Glu Pro Ser
            180                 185                 190

Asp Gly Arg Lys Glu Lys Ile Glu Trp Ala Asp Tyr Arg Met Asn
            195                 200                 205

Gln Lys Phe Ala Ala Lys Ile Leu Glu Ile Tyr Lys Pro Gly Asp Ile
210                 215                 220

Val Ile Ile His Asp Tyr Phe Leu Met Leu Pro Ser Met Leu Arg
225                 230                 235                 240

Gln Ala Val Pro Asn Met Tyr Ile Ser Phe Tyr Leu His Cys Pro Phe
                245                 250                 255

Pro Ser Ser Glu Phe Leu Arg Cys Leu Pro Arg Arg Arg Glu Val Leu
            260                 265                 270

Glu Gly Ile Leu Gly Ser Asn Leu Val Gly Phe Gln Ser Tyr Ser Tyr
            275                 280                 285

Ser Arg His Phe Leu Ser Cys Cys Thr Arg Ile Leu Gly Phe Pro Ser
290                 295                 300

Asp Thr Leu Gly Val Asp Ala Tyr Gly Ser Arg Val Gln Val Gly Val
305                 310                 315                 320

Phe Pro Ile Gly Ile Asp Ala Ala Lys Val Glu Lys Leu Ala Trp Ala
                325                 330                 335

Ser Ser Val Asp Glu Lys Tyr Asp Ala Leu Lys Lys Met Tyr Ala Gly
            340                 345                 350

Lys Lys Ile Ile Val Gly Arg Asp Arg Leu Asp Ser Val Arg Gly Val
            355                 360                 365

Val Gln Lys Leu Gln Ala Phe Asp Arg Phe Leu Glu Met Tyr Ser Glu
370                 375                 380

Trp Arg Glu Lys Val Val Leu Ile Gln Val Thr Ser Pro Thr Asn Lys
385                 390                 395                 400

Val Ala Asp Lys Glu Asp Gly Glu His Lys Thr Ser Thr Arg Val Asn
                405                 410                 415

Glu Leu Val Met Gln Ile Asn Gly Lys Tyr Gly Ser Leu Gly Phe Ser
            420                 425                 430

Pro Val Gln His Tyr Pro Gln Tyr Ile Asn Gln Asp Glu Tyr Phe Ala
            435                 440                 445

Leu Leu Arg Ala Ala Asp Ile Gly Leu Ile Thr Ser Val Arg Asp Gly
450                 455                 460

Met Asn Thr Thr Ser Leu Glu Tyr Val Val Cys Gln Lys Asp Gly His
465                 470                 475                 480

Gly Pro Leu Ile Leu Ser Glu Phe Ser Gly Thr Ala Ala Ser Leu Ser
                485                 490                 495

Asp Ala Ile His Ile Asn Pro Trp Asp Leu Thr Asp Val Ala Gly Lys
```

```
            500                 505                 510
Ile Asn Gly Ala Leu Thr Met Pro Asp Asp Ala Arg Ser Lys Met Gln
            515                 520                 525

Ser Arg Leu Tyr Glu His Val Thr Gln Thr Val Gln Ser Trp Ile
        530                 535                 540

Thr Lys Phe Ile Arg Arg Ile His Ser Val Leu Gly Asp Lys Ser Ile
545                 550                 555                 560

Gln His Ser Thr Pro Leu Leu Asp Arg Ala Leu Leu Leu Ser Gln Tyr
                565                 570                 575

Arg Ala Ala Ser Lys Arg Ile Phe Met Phe Asp Tyr Asp Gly Thr Leu
            580                 585                 590

Thr Pro Ile Val Arg Glu Pro Ser Ala Val Pro Ser Glu Lys Leu
        595                 600                 605

Leu Glu Ser Leu Lys Ile Leu Ala Ala Glu Pro Arg Asn Ser Val Trp
610                 615                 620

Ile Ile Ser Gly Arg Asp Gln Glu Phe Leu Thr Gln His Leu Gly His
625                 630                 635                 640

Ile Pro Glu Leu Gly Phe Ser Ala Glu His Gly Ser Phe Met Arg Asp
                645                 650                 655

Pro Gly Ser Gln Glu Trp Ile Asn Leu Ala Asp Lys Phe Asp Met Gly
            660                 665                 670

Trp Gln Asn Glu Val Ile Asp Val Phe Gln Lys Tyr Thr Asp Lys Val
        675                 680                 685

Thr Gly Ser Phe Ile Glu Arg Lys Arg Cys Ala Ile Thr Trp His Tyr
690                 695                 700

Arg Leu Ala Asp Pro Glu Gln Gly Leu His Met Ser Arg Val Ala His
705                 710                 715                 720

Lys Glu Val Glu Glu Thr Val Ala Lys Lys Trp Asp Val Glu Val Met
                725                 730                 735

Ala Gly Lys Ala Asn Ile Glu Val Arg Pro Thr Phe Ile Asn Lys Gly
            740                 745                 750

Glu Ile Val Lys Arg Leu Ile Ser Arg Tyr His Asn Pro Gly Leu Val
        755                 760                 765

Ala Asp Glu Gly Asp Arg Asn Ala Gly Arg Ile Glu Phe Ala Leu Cys
770                 775                 780

Ser Gly Asp Asp Phe Thr Asp Glu Asp Met Phe Arg Ser Leu Asn Gly
785                 790                 795                 800

Val Ser Gly Ser Val Leu Asp Ala Asp His Val Phe Thr Val Thr Val
                805                 810                 815

Gly Pro Ser Thr Lys Val Thr Leu Ala Arg Trp His Leu Leu Glu Pro
            820                 825                 830

Ala Asp Val Asp Cys Val Thr Leu Leu Ser Glu Gln Lys Gly His
        835                 840                 845

Leu Ala Leu Glu Arg Met Gly Glu Val Asn Leu Ala Ala Leu Ser Ser
850                 855                 860

Val Glu Gly His Ile Pro Thr Ala
865                 870
```

<210> SEQ ID NO 3
<211> LENGTH: 896
<212> TYPE: PRT
<213> ORGANISM: Saccharomyces cerevisiae

<400> SEQUENCE: 3

-continued

```
Met Thr Thr Thr Ala Gln Asp Asn Ser Pro Lys Lys Arg Gln Arg Ile
1               5                   10                  15

Ile Asn Cys Val Thr Gln Leu Pro Tyr Lys Ile Gln Leu Gly Glu Ser
            20                  25                  30

Asn Asp Asp Trp Lys Ile Ser Ala Thr Thr Gly Asn Ser Ala Leu Phe
        35                  40                  45

Ser Ser Leu Glu Tyr Leu Gln Phe Asp Ser Thr Glu Tyr Glu Gln His
    50                  55                  60

Val Val Gly Trp Thr Gly Glu Ile Thr Arg Thr Glu Arg Asn Leu Phe
65                  70                  75                  80

Thr Arg Glu Ala Lys Glu Lys Pro Gln Asp Leu Asp Asp Pro Leu
                85                  90                  95

Tyr Leu Thr Lys Glu Gln Ile Asn Gly Leu Thr Thr Thr Leu Gln Asp
            100                 105                 110

His Met Lys Ser Asp Lys Glu Ala Lys Thr Asp Thr Thr Gln Thr Ala
            115                 120                 125

Pro Val Thr Asn Asn Val His Pro Val Trp Leu Leu Arg Lys Asn Gln
    130                 135                 140

Ser Arg Trp Arg Asn Tyr Ala Glu Lys Val Ile Trp Pro Thr Phe His
145                 150                 155                 160

Tyr Ile Leu Asn Pro Ser Asn Glu Gly Glu Gln Lys Asn Trp Trp
                165                 170                 175

Tyr Asp Tyr Val Lys Phe Asn Glu Ala Tyr Ala Gln Lys Ile Gly Glu
            180                 185                 190

Val Tyr Arg Lys Gly Asp Ile Ile Trp Ile His Asp Tyr Tyr Leu Leu
    195                 200                 205

Leu Leu Pro Gln Leu Leu Arg Met Lys Phe Asn Asp Glu Ser Ile Ile
    210                 215                 220

Ile Gly Tyr Phe His His Ala Pro Trp Pro Ser Asn Glu Tyr Phe Arg
225                 230                 235                 240

Cys Leu Pro Arg Arg Lys Gln Ile Leu Asp Gly Leu Val Gly Ala Asn
            245                 250                 255

Arg Ile Cys Phe Gln Asn Glu Ser Phe Ser Arg His Phe Val Ser Ser
            260                 265                 270

Cys Lys Arg Leu Leu Asp Ala Thr Ala Lys Lys Ser Lys Asn Ser Ser
    275                 280                 285

Asn Ser Asp Gln Tyr Gln Val Ser Val Tyr Gly Gly Asp Val Leu Val
    290                 295                 300

Asp Ser Leu Pro Ile Gly Val Asn Thr Thr Gln Ile Leu Lys Asp Ala
305                 310                 315                 320

Phe Thr Lys Asp Ile Asp Ser Lys Val Leu Ser Ile Lys Gln Ala Tyr
            325                 330                 335

Gln Asn Lys Lys Ile Ile Ile Gly Arg Asp Arg Leu Asp Ser Val Arg
            340                 345                 350

Gly Val Val Gln Lys Leu Arg Ala Phe Glu Thr Phe Leu Ala Met Tyr
    355                 360                 365

Pro Glu Trp Arg Asp Gln Val Val Leu Ile Gln Val Ser Ser Pro Thr
    370                 375                 380

Ala Asn Arg Asn Ser Pro Gln Thr Ile Arg Leu Glu Gln Gln Val Asn
385                 390                 395                 400

Glu Leu Val Asn Ser Ile Asn Ser Glu Tyr Gly Asn Leu Asn Phe Ser
            405                 410                 415

Pro Val Gln His Tyr Tyr Met Arg Ile Pro Lys Asp Val Tyr Leu Ser
```

```
            420                 425                 430
Leu Leu Arg Val Ala Asp Leu Cys Leu Ile Thr Ser Val Arg Asp Gly
            435                 440                 445

Met Asn Thr Thr Ala Leu Glu Tyr Val Thr Val Lys Ser His Met Ser
            450                 455                 460

Asn Phe Leu Cys Tyr Gly Asn Pro Leu Ile Leu Ser Glu Phe Ser Gly
465                 470                 475                 480

Ser Ser Asn Val Leu Lys Asp Ala Ile Val Val Asn Pro Trp Asp Ser
                485                 490                 495

Val Ala Val Ala Lys Ser Ile Asn Met Ala Leu Lys Leu Asp Lys Glu
            500                 505                 510

Glu Lys Ser Asn Leu Glu Ser Lys Leu Trp Lys Glu Val Pro Thr Ile
            515                 520                 525

Gln Asp Trp Thr Asn Lys Phe Leu Ser Ser Leu Lys Glu Gln Ala Ser
            530                 535                 540

Ser Asn Asp Asp Met Glu Arg Lys Met Thr Pro Ala Leu Asn Arg Pro
545                 550                 555                 560

Val Leu Leu Glu Asn Tyr Lys Gln Ala Lys Arg Leu Phe Leu Phe
                565                 570                 575

Asp Tyr Asp Gly Thr Leu Thr Pro Ile Val Lys Asp Pro Ala Ala Ala
            580                 585                 590

Ile Pro Ser Ala Arg Leu Tyr Thr Ile Leu Gln Lys Leu Cys Ala Asp
            595                 600                 605

Pro His Asn Gln Ile Trp Ile Ile Ser Gly Arg Asp Gln Lys Phe Leu
            610                 615                 620

Asn Lys Trp Leu Gly Gly Lys Leu Pro Gln Leu Gly Leu Ser Ala Glu
625                 630                 635                 640

His Gly Cys Phe Met Lys Asp Val Ser Cys Gln Asp Trp Val Asn Leu
                645                 650                 655

Thr Glu Lys Val Asp Met Ser Trp Gln Val Arg Val Asn Glu Val Met
            660                 665                 670

Glu Glu Phe Thr Thr Arg Thr Pro Gly Ser Phe Ile Glu Arg Lys Lys
            675                 680                 685

Val Ala Leu Thr Trp His Tyr Arg Arg Thr Val Pro Glu Leu Gly Glu
            690                 695                 700

Phe His Ala Lys Glu Leu Lys Glu Lys Leu Leu Ser Phe Thr Asp Asp
705                 710                 715                 720

Phe Asp Leu Glu Val Met Asp Gly Lys Ala Asn Ile Glu Val Arg Pro
                725                 730                 735

Arg Phe Val Asn Lys Gly Glu Ile Val Lys Arg Leu Val Trp His Gln
                740                 745                 750

His Gly Lys Pro Gln Asp Met Leu Lys Gly Ile Ser Glu Lys Leu Pro
            755                 760                 765

Lys Asp Glu Met Pro Asp Phe Val Leu Cys Leu Gly Asp Asp Phe Thr
            770                 775                 780

Asp Glu Asp Met Phe Arg Gln Leu Asn Thr Ile Glu Thr Cys Trp Lys
785                 790                 795                 800

Glu Lys Tyr Pro Asp Gln Lys Asn Gln Trp Gly Asn Tyr Gly Phe Tyr
                805                 810                 815

Pro Val Thr Val Gly Ser Ala Ser Lys Lys Thr Val Ala Lys Ala His
            820                 825                 830

Leu Thr Asp Pro Gln Gln Val Leu Glu Thr Leu Gly Leu Leu Val Gly
            835                 840                 845
```

```
Asp Val Ser Leu Phe Gln Ser Ala Gly Thr Val Asp Leu Asp Ser Arg
            850                 855                 860

Gly His Val Lys Asn Ser Glu Ser Ser Leu Lys Ser Lys Leu Ala Ser
865                 870                 875                 880

Lys Ala Tyr Val Met Lys Arg Ser Ala Ser Tyr Thr Gly Ala Lys Val
                885                 890                 895

<210> SEQ ID NO 4
<211> LENGTH: 945
<212> TYPE: PRT
<213> ORGANISM: Aspergillus flavus

<400> SEQUENCE: 4

Met Ser Ser Glu Gln Arg Thr Thr Pro Ala Lys Ile Pro Ser Asp Gln
1               5                   10                  15

Pro Asp Pro Val Leu Val Gly Pro Val Lys Val Leu Gly Glu Glu
                20                  25                  30

Ala Tyr Thr Lys Ala Ser Thr Ala Thr Pro Ile Pro Gly Gly Glu Lys
                35                  40                  45

Lys Gln Ser Phe Thr Thr Asp Ala Pro Ser Tyr Phe Ser Lys Thr Pro
        50                  55                  60

Gly Glu Lys Met Ser Ser Glu Ser Ser Asn Ala Thr Pro Thr Thr Pro
65              70                  75                  80

Ala Gln Ala Ala Lys Asp Ala Arg Ser Arg Ile Glu Leu Leu Arg Arg
                85                  90                  95

Leu Ser Leu Arg Glu Thr Pro Lys Val Leu Glu Ala Asp Leu Arg Gln
            100                 105                 110

Gln His Pro Gly Leu Arg Leu Ser Gly Arg Ile Ile Ser Ala Ala Phe
        115                 120                 125

Cys Ile Pro Tyr Lys Val Tyr Tyr Arg Arg Glu Ser Ser Trp Glu Leu
130                 135                 140

Lys Pro Arg Pro Gly Thr Ser Ala Leu Phe Asp Ser Leu Ala Tyr Leu
145                 150                 155                 160

Gly Ser Glu Glu Thr Asn Trp Ser His Thr Leu Val Gly Trp Thr Gly
                165                 170                 175

Glu Val Glu Pro Val Pro Glu Asp Thr Val Pro Leu Gln Gln Ile Pro
            180                 185                 190

Ile Asn Thr Ser Ala Lys Leu Pro Ala Ala Thr Asn Gly Thr Ala Lys
        195                 200                 205

Pro Leu Asn Lys Ala Ala Ala Pro Val Pro Val Asp Ala Asn Gln Arg
    210                 215                 220

Pro Pro Ser His Pro Leu Leu Asp Gly Phe Thr Val Ser Gln Asp Asp
225                 230                 235                 240

Arg Ser Arg Leu Asp Ala Gln Leu Ser Ser Gly Arg Tyr Gly Lys Ile
                245                 250                 255

Ala Pro Val Trp Leu Ser Ala Glu Thr Glu Ile Pro Glu Asp Thr Ile
            260                 265                 270

Phe Leu Glu Asp Gln Gly Arg Trp Arg Arg Tyr Ala Glu Arg Glu Leu
        275                 280                 285

Tyr Pro Leu Leu His Tyr Lys Gln His Gly Pro Thr Asp Gly Arg Ser
    290                 295                 300

Glu Arg Asn Trp Trp Ala Asp Tyr Val Arg Met Asn Arg Leu Phe Ala
305                 310                 315                 320

Asp Arg Ile Leu Lys Glu Tyr Gln Glu Gly Asp Ile Val Trp Ile His
```

```
                    325                 330                 335
Asp Tyr His Leu Phe Leu Pro Ser Met Leu Arg Gln Arg Ile Pro
            340                 345                 350
Asn Ile Tyr Ile Gly Phe Phe Leu His Ala Pro Phe Pro Ser Ser Glu
            355                 360                 365
Phe Met Arg Cys Leu Ala Lys Arg Lys Glu Val Leu Thr Gly Val Leu
370                 375                 380
Gly Ala Asn Met Ile Gly Phe Gln Thr Phe Ser Tyr Ser Arg His Phe
385                 390                 395                 400
Ser Ser Cys Cys Thr Arg Val Leu Gly Phe Asp Ser Asn Ser Ala Gly
                    405                 410                 415
Val Asp Ala Tyr Gly Ala His Val Ala Val Asp Val Phe Pro Ile Gly
                    420                 425                 430
Ile Asp Ala Lys Ala Ile Gln Asn Ile Ala Phe Gly Ala Ser Glu Ile
                    435                 440                 445
Glu Asn Ala Val Thr Gly Ile Arg Lys Leu Tyr Ala Gly Lys Lys Ile
            450                 455                 460
Ile Val Gly Arg Asp Arg Leu Asp Ser Val Arg Gly Val Ala Gln Lys
465                 470                 475                 480
Leu Gln Ser Phe Glu Val Phe Leu Glu Arg Tyr Pro Glu Trp Arg Asp
                    485                 490                 495
Lys Val Val Leu Ile Gln Val Thr Ser Pro Thr Ser Val Glu Glu Glu
            500                 505                 510
Lys Glu Glu Asn Lys Ile Ala Ser Gln Ile Ser Asn Leu Val Ser Thr
            515                 520                 525
Ile Asn Gly Arg Phe Gly Ser Leu Ser Phe Ser Pro Val Lys Tyr Tyr
    530                 535                 540
Pro Gln Tyr Leu Ser Gln His Glu Tyr Phe Ala Leu Leu Arg Val Ala
545                 550                 555                 560
Asp Val Gly Leu Ile Thr Thr Val Arg Asp Gly Met Asn Thr Thr Ser
                    565                 570                 575
Leu Glu Tyr Ile Ile Cys Gln Gln Ser His Gly Pro Leu Ile Leu
            580                 585                 590
Ser Glu Phe Ser Gly Thr Ala Gly Thr Leu Ser Ser Ala Ile His Ile
    595                 600                 605
Asn Pro Trp Asp Thr Ala Gly Val Ala Gly Ala Ile Asn Gln Ala Leu
    610                 615                 620
Thr Met Ser Pro Glu Ser Lys Lys Ala Ser His Gln Lys Leu Tyr Lys
625                 630                 635                 640
His Val Thr Thr Asn Thr Val Ser Ala Trp Ser Thr Gln Tyr Leu Ser
                    645                 650                 655
Arg Leu Leu Thr Asn Leu Ser Ser Phe Asp Gln Ser Val Ala Thr Pro
            660                 665                 670
Ala Leu Asp Arg Ala Lys Leu Leu Lys Gln Tyr Arg Lys Ala Arg Lys
            675                 680                 685
Arg Leu Phe Met Phe Asp Tyr Asp Gly Thr Leu Thr Pro Ile Val Lys
            690                 695                 700
Asp Pro Gln Ala Ala Ile Pro Ser Asp Arg Val Leu Arg Thr Ile Lys
705                 710                 715                 720
Thr Leu Ala Ala Asp Ser Arg Asn Ala Val Trp Ile Ile Ser Gly Arg
                    725                 730                 735
Asp Gln Ala Phe Leu Asp Glu Trp Met Gly His Ile Pro Glu Leu Gly
            740                 745                 750
```

Leu Ser Ala Glu His Gly Cys Phe Ile Arg Lys Pro Arg Ser Asp Asp
        755                 760                 765

Trp Glu Asn Leu Ala Glu Arg Ser Asn Met Gly Trp Gln Lys Glu Val
    770                 775                 780

Met Glu Ile Phe Gln His Tyr Thr Glu Arg Thr Gln Gly Ser Phe Ile
785                 790                 795                 800

Glu Arg Lys Arg Val Ala Leu Thr Trp His Tyr Arg Arg Ala Asp Pro
                805                 810                 815

Glu Tyr Gly Ala Phe Gln Ala Arg Glu Cys Arg Lys His Leu Glu Glu
                820                 825                 830

Thr Val Gly Lys Arg Trp Asp Val Glu Val Met Ala Gly Lys Ala Asn
                835                 840                 845

Leu Glu Val Arg Pro Thr Phe Val Asn Lys Gly Phe Ile Ala Ser Arg
        850                 855                 860

Leu Val Asn Glu Tyr Gly Thr Gly Pro Gly Gln Ala Pro Glu Phe Ile
865                 870                 875                 880

Phe Cys Ser Gly Asp Asp Phe Thr Asp Glu Asp Met Phe Arg Ala Leu
                885                 890                 895

Gln Lys Phe Asp Leu Pro Gln Asp His Val Tyr Ser Val Thr Val Gly
                900                 905                 910

Ala Ser Ser Lys Gln Thr Ser Ala Ser Trp His Leu Leu Glu Pro Ala
                915                 920                 925

Asp Val Ile Glu Thr Val Thr Met Leu Asn Ser Ser Thr Gln Asp
        930                 935                 940

Tyr
945

<210> SEQ ID NO 5
<211> LENGTH: 945
<212> TYPE: PRT
<213> ORGANISM: Aspergillus oryzae

<400> SEQUENCE: 5

Met Ser Ser Glu Gln Arg Thr Thr Pro Ala Lys Ile Pro Ser Asp Gln
1               5                   10                  15

Pro Asp Pro Val Leu Val Gly Pro Val Lys Val Leu Gly Glu Glu
            20                  25                  30

Ala Tyr Thr Lys Ala Ser Thr Ala Thr Pro Ile Pro Gly Gly Glu Lys
            35                  40                  45

Lys Gln Ser Phe Thr Thr Asp Ala Pro Ser Tyr Phe Ser Lys Thr Pro
    50                  55                  60

Gly Glu Lys Met Ser Ser Glu Ser Ser Asn Ala Thr Pro Thr Thr Pro
65              70                  75                  80

Ala Gln Ala Ala Lys Asp Ala Arg Ser Arg Ile Glu Leu Leu Arg Arg
                85                  90                  95

Leu Ser Leu Arg Glu Thr Pro Lys Val Leu Glu Ala Asp Leu Arg Gln
            100                 105                 110

Gln His Pro Gly Leu Arg Leu Ser Gly Arg Ile Ile Ser Ala Ala Phe
        115                 120                 125

Cys Ile Pro Tyr Lys Val Tyr Tyr Arg Arg Glu Ser Ser Trp Glu Leu
    130                 135                 140

Lys Pro Arg Pro Gly Thr Ser Ala Leu Phe Asp Ser Leu Ala Tyr Leu
145                 150                 155                 160

Gly Ser Glu Glu Thr Asn Trp Ser His Thr Leu Val Gly Trp Thr Gly

```
                        165                 170                 175
Glu Val Glu Pro Val Pro Glu Asp Thr Val Pro Leu Gln Gln Ile Pro
                180                 185                 190
Ile Asn Thr Ser Ala Lys Leu Pro Ala Ala Thr Asn Gly Thr Ala Lys
            195                 200                 205
Pro Leu Asn Lys Ala Ala Ala Pro Val Pro Val Asp Ala Asn Gln Arg
        210                 215                 220
Pro Pro Ser His Pro Leu Leu Asp Gly Phe Thr Val Ser Gln Asp Asp
225                 230                 235                 240
Arg Ser Arg Leu Asp Ala Gln Leu Ser Ser Gly Arg Tyr Gly Lys Ile
                245                 250                 255
Ala Pro Val Trp Leu Ser Ala Glu Thr Glu Ile Pro Glu Asp Thr Ile
                260                 265                 270
Phe Leu Glu Asp Gln Gly Arg Trp Arg Tyr Ala Glu Arg Glu Leu
            275                 280                 285
Tyr Pro Leu Leu His Tyr Lys Gln His Gly Pro Thr Asp Gly Arg Ser
        290                 295                 300
Glu Arg Asn Trp Trp Ala Asp Tyr Val Arg Met Asn Arg Leu Phe Ala
305                 310                 315                 320
Asp Arg Ile Leu Lys Glu Tyr Gln Glu Gly Asp Ile Val Trp Ile His
                325                 330                 335
Asp Tyr His Leu Phe Leu Leu Pro Ser Met Leu Arg Gln Arg Ile Pro
                340                 345                 350
Asn Ile Tyr Ile Gly Phe Phe Leu His Ala Pro Phe Pro Ser Ser Glu
            355                 360                 365
Phe Met Arg Cys Leu Ala Lys Arg Lys Glu Val Leu Thr Gly Val Leu
        370                 375                 380
Gly Ala Asn Met Ile Gly Phe Gln Thr Phe Ser Tyr Ser Arg His Phe
385                 390                 395                 400
Ser Ser Cys Cys Thr Arg Val Leu Gly Phe Asp Ser Asn Ser Ala Gly
                405                 410                 415
Val Asp Ala Tyr Gly Ala His Val Ala Val Asp Val Phe Pro Ile Gly
                420                 425                 430
Ile Asp Ala Lys Ala Ile Gln Asn Ile Ala Phe Gly Ala Ser Glu Ile
            435                 440                 445
Glu Asn Ala Val Thr Gly Ile Arg Lys Leu Tyr Ala Gly Lys Lys Ile
        450                 455                 460
Ile Val Gly Arg Asp Arg Leu Asp Ser Val Arg Gly Val Ala Gln Lys
465                 470                 475                 480
Leu Gln Ser Phe Glu Val Phe Leu Glu Arg Tyr Pro Glu Trp Arg Asp
                485                 490                 495
Lys Val Val Leu Ile Gln Val Thr Ser Pro Thr Ser Val Glu Glu Glu
                500                 505                 510
Lys Glu Glu Asn Lys Ile Ala Ser Gln Ile Ser Asn Leu Val Ser Thr
            515                 520                 525
Ile Asn Gly Arg Phe Gly Ser Leu Ser Phe Ser Pro Val Lys Tyr Tyr
        530                 535                 540
Pro Gln Tyr Leu Ser Gln His Glu Tyr Phe Ala Leu Leu Arg Val Ala
545                 550                 555                 560
Asp Val Gly Leu Ile Thr Thr Val Arg Asp Gly Met Asn Thr Thr Ser
                565                 570                 575
Leu Glu Tyr Ile Ile Cys Gln Gln Ser His Gly Pro Leu Ile Leu
            580                 585                 590
```

```
Ser Glu Phe Ser Gly Thr Ala Gly Thr Leu Ser Ser Ala Ile His Ile
        595                 600                 605

Asn Pro Trp Asp Thr Ala Gly Val Ala Gly Ala Ile Asn Gln Ala Leu
        610                 615                 620

Thr Met Ser Pro Glu Ser Lys Lys Ala Ser His Gln Lys Leu Tyr Lys
625                 630                 635                 640

His Val Thr Thr Asn Thr Val Ser Ala Trp Ser Thr Gln Tyr Leu Ser
                645                 650                 655

Arg Leu Leu Thr Asn Leu Ser Ser Phe Asp Gln Ser Val Ala Thr Pro
                660                 665                 670

Ala Leu Asp Arg Ala Lys Leu Leu Lys Gln Tyr Arg Lys Ala Arg Lys
            675                 680                 685

Arg Leu Phe Met Phe Asp Tyr Asp Gly Thr Leu Thr Pro Ile Val Lys
        690                 695                 700

Asp Pro Gln Ala Ala Ile Pro Ser Asp Arg Val Leu Arg Thr Ile Lys
705                 710                 715                 720

Thr Leu Ala Ala Asp Ser Arg Asn Ala Val Trp Ile Ile Ser Gly Arg
                725                 730                 735

Asp Gln Ala Phe Leu Asp Glu Trp Met Gly His Ile Pro Glu Leu Gly
                740                 745                 750

Leu Ser Ala Glu His Gly Cys Phe Ile Arg Lys Pro Arg Ser Asp Asp
            755                 760                 765

Trp Glu Asn Leu Ala Glu Arg Ser Asn Met Gly Trp Gln Lys Glu Val
        770                 775                 780

Met Glu Ile Phe Gln His Tyr Thr Glu Arg Thr Gln Gly Ser Phe Ile
785                 790                 795                 800

Glu Arg Lys Arg Val Ala Leu Thr Trp His Tyr Arg Arg Ala Asp Pro
                805                 810                 815

Glu Tyr Gly Ala Phe Gln Ala Arg Glu Cys Arg Lys His Leu Glu Glu
            820                 825                 830

Thr Val Gly Lys Arg Trp Asp Val Glu Val Met Ala Gly Lys Ala Asn
        835                 840                 845

Leu Glu Val Arg Pro Thr Phe Val Asn Lys Gly Phe Ile Ala Ser Arg
850                 855                 860

Leu Val Asn Glu Tyr Gly Thr Gly Pro Gly Gln Ala Pro Glu Phe Ile
                870                 875                 880
865

Phe Cys Ser Gly Asp Asp Phe Thr Asp Glu Asp Met Phe Arg Ala Leu
                885                 890                 895

Gln Lys Phe Asp Leu Pro Gln Asp His Val Tyr Ser Val Thr Val Gly
            900                 905                 910

Ala Ser Lys Gln Thr Ser Ala Ser Trp His Leu Leu Glu Pro Ala
        915                 920                 925

Asp Val Ile Glu Thr Val Thr Met Leu Asn Ser Ser Ser Thr Gln Asp
        930                 935                 940

Tyr
945

<210> SEQ ID NO 6
<211> LENGTH: 948
<212> TYPE: PRT
<213> ORGANISM: Aspergillus clavatus

<400> SEQUENCE: 6

Met Ser Ala Ser Gln Asp Ser Pro Ser Ala Lys Val Leu Asp Gly Gln
```

-continued

```
1               5                   10                  15
Pro Asn Pro Val Ile Val Gly Pro Gly Met Lys Ser Leu Gly Glu Asp
                20                  25                  30

Ala Tyr Thr Gln Ala Ala Asn Val Thr Pro Ser Leu Asp Thr Asp Lys
                35                  40                  45

Lys His Pro Val Asp Ser Asp Ala Pro Ser Tyr Phe Ala Asn Ile Pro
            50                  55                  60

Asp Thr Gln Pro Ser Ala Asp Val Asn Ser Pro Ala Thr Pro Ala Asp
65                  70                  75                  80

Ala Ala Lys Ser Ala Lys Ser Pro Ile Glu Leu Leu His Arg Leu Ser
                85                  90                  95

Leu Asn Arg Thr Pro Leu Val Pro Asp Phe Asp Pro Arg Glu Gln Tyr
            100                 105                 110

Pro Gly Leu Asn Leu Thr Gly Arg Phe Ile Ser Ala Ala Phe Cys Ile
            115                 120                 125

Pro Tyr Lys Val Tyr Arg Pro Gly Ser Asp Trp Glu Leu Lys Pro
            130                 135                 140

Arg Pro Gly Thr Ser Ala Leu Phe Asp Ser Phe Ala Tyr Leu Gly Ser
145                 150                 155                 160

Glu Glu Thr Lys Trp Ser His Thr Leu Val Gly Trp Thr Gly Glu Val
                165                 170                 175

Glu Pro Ile Gln Glu Thr Pro Ala Ser Leu Gln Gln Ile Pro Val Asn
            180                 185                 190

Ala Gly Ala Lys Leu Pro Pro Ala Leu Asn Gly Val Ala Val Pro Leu
            195                 200                 205

Ser Lys Ala Ala Ala Pro Val Pro Val Asp Ser Ser Gln Arg Pro Pro
210                 215                 220

Ser His Pro Leu Leu Glu Gly Phe Thr Val Pro Gln Glu Asp Arg Ala
225                 230                 235                 240

Arg Leu Asp Gly Gln Leu Gly Ser Gly Arg Tyr Gly Lys Ile Ala Pro
                245                 250                 255

Val Trp Leu Ser Asp Glu Ser Glu Pro Glu Glu Ser Ser Thr Ile
                260                 265                 270

Phe Leu Glu Asp Gln Gly Lys Trp Arg Arg Tyr Ala Glu Lys Glu Leu
            275                 280                 285

Tyr Pro Leu Leu His Tyr Lys Gln His Gly Pro Thr Asp Gly Arg Ser
            290                 295                 300

Glu Arg Lys Trp Trp Gly Asp Tyr Val Arg Met Asn Arg Leu Phe Ala
305                 310                 315                 320

Asp Arg Ile Leu Glu Glu Tyr Lys Glu Gly Asp Ile Val Trp Ile His
                325                 330                 335

Asp Tyr His Leu Phe Leu Leu Pro Ser Leu Leu Arg Gln Arg Ile Pro
            340                 345                 350

Asn Ile Tyr Ile Gly Phe Phe Leu His Ala Pro Phe Pro Ser Ser Glu
            355                 360                 365

Phe Met Arg Cys Leu Ala Lys Arg Lys Glu Val Leu Thr Gly Val Leu
            370                 375                 380

Gly Ser Asn Met Ile Gly Phe Gln Thr Phe Ser Tyr Ser Arg His Phe
385                 390                 395                 400

Ser Ser Cys Cys Thr Arg Val Leu Gly Phe Glu Ser Asn Ser Ala Gly
                405                 410                 415

Val Asp Ala Tyr Gly Ala His Val Ala Val Asp Val Phe Pro Ile Gly
            420                 425                 430
```

```
Ile Asp Val Lys Ala Ile Gln Lys Ala Ala Phe Gly Pro Ala Asn Ile
        435                 440                 445

Glu Asn Ala Val Val Ala Leu Arg Asn Leu Tyr Ala Gly Lys Lys Ile
450                 455                 460

Ile Val Gly Arg Asp Arg Leu Asp Ser Val Arg Gly Val Ala Gln Lys
465                 470                 475                 480

Leu Gln Ala Phe Glu Ala Phe Leu Glu Arg Tyr Pro Glu Trp Arg Asp
                485                 490                 495

Lys Val Val Leu Ile Gln Val Thr Ser Pro Thr Ser Val Glu Glu Glu
                500                 505                 510

Lys Glu Asp Pro Glu Asn Lys Ile Ala Ser Gln Ile Ser Asn Leu Val
                515                 520                 525

Ser Thr Ile Asn Gly Arg Phe Gly Ser Ile Ser Phe Ser Pro Val Lys
530                 535                 540

Tyr Tyr Pro Gln Tyr Leu Ser Gln His Glu Tyr Phe Ala Leu Leu Arg
545                 550                 555                 560

Val Ala Asp Val Gly Leu Ile Thr Thr Val Arg Asp Gly Met Asn Thr
                565                 570                 575

Thr Ser Leu Glu Tyr Ile Leu Cys Gln Gln Asn Thr His Ser Pro Leu
            580                 585                 590

Ile Leu Ser Glu Phe Ser Gly Thr Ala Gly Pro Leu Ser Ser Ala Ile
            595                 600                 605

His Ile Asn Pro Trp Asp Thr Ile Gly Val Ala Glu Ala Ile Asn Glu
        610                 615                 620

Ala Leu Thr Met Ser Pro Glu Glu Lys Arg Leu Gln His Val His Leu
625                 630                 635                 640

Tyr Lys His Val Thr Thr Asn Thr Val Leu Thr Trp Ser Asn Gln Phe
                645                 650                 655

Val Thr Arg Leu Leu Thr Asn Leu Ser Ser Phe Asp Gln Ser Val Ala
                660                 665                 670

Thr Pro Ala Leu Asp Arg Ala Thr Val Leu Lys Gln Tyr Arg Lys Ala
            675                 680                 685

Arg Lys Arg Leu Phe Met Phe Asp Tyr Asp Gly Thr Leu Thr Pro Ile
        690                 695                 700

Val Lys Asp Pro Gln Ala Ala Ile Pro Ser Asp Arg Val Leu Arg Asn
705                 710                 715                 720

Ile Lys Thr Leu Ala Ala Asp Pro Arg Asn Ala Val Trp Ile Ile Ser
                725                 730                 735

Gly Arg Asp Gln Ala Phe Leu Asp Glu Trp Met Gly His Ile Pro Glu
                740                 745                 750

Leu Gly Leu Ser Ala Glu His Gly Cys Phe Ile Arg Lys Pro Arg Ser
            755                 760                 765

Asp Asp Trp Glu Asn Leu Ala Glu Ser Ser Asp Met Gly Trp Gln Lys
        770                 775                 780

Glu Val Val Glu Val Phe Gln His Phe Thr Glu Arg Thr Gln Gly Ser
785                 790                 795                 800

Phe Ile Glu Arg Lys Arg Val Ala Leu Thr Trp His Tyr Arg Arg Ala
                805                 810                 815

Asp Pro Glu Tyr Gly Ala Phe Gln Ala Arg Glu Cys Arg Lys Gln Leu
            820                 825                 830

Glu Glu Thr Val Ala Lys Arg Trp Asp Val Glu Val Met Ala Gly Lys
        835                 840                 845
```

Ala Asn Leu Glu Val Arg Pro Thr Phe Val Asn Lys Gly Phe Ile Ala
            850                 855                 860

Ser Arg Leu Val Asp Glu Tyr Gly Thr Gly Pro Gly Gln Ala Pro Glu
865                 870                 875                 880

Phe Val Leu Cys Leu Gly Asp Asp Phe Thr Asp Glu Asp Met Phe Arg
                885                 890                 895

Ala Leu Lys Lys Ala Asn Leu Pro Ala Asp His Val Tyr Ser Val Thr
            900                 905                 910

Val Gly Ala Ser Ser Lys Gln Thr Glu Ala Ser Trp His Leu Leu Glu
            915                 920                 925

Pro Ala Asp Val Ile Gly Thr Ile Ser Val Leu Asn Asn Ser Ser Ser
930                 935                 940

Ala Gln Glu Tyr
945

<210> SEQ ID NO 7
<211> LENGTH: 944
<212> TYPE: PRT
<213> ORGANISM: Talaromyces stipitatus

<400> SEQUENCE: 7

Met Ala Ser Glu Gln Gly Ala Pro Asp Lys Ile Pro Pro Asn Gln Pro
1               5                   10                  15

Asn Pro Val Ile Val Gly Pro Gly Leu Ser Ala Leu Gly Glu Glu Ala
            20                  25                  30

Tyr Val Asp Ala Ser Thr Ala Thr Pro Ala Val Val Pro Ala Thr Thr
            35                  40                  45

Thr Thr Ala Asn Ala Asp Gly Ala Ala Asp Ser Tyr Phe Ser Gln Val
50                  55                  60

Pro Gly Thr Ala Thr Ala Ile Lys Asp Ala Tyr Ala Lys Ser Pro Met
65                  70                  75                  80

Ser Pro Ala Asp Ala Ala Ser Gly Val Thr Ser Gly Pro Glu Leu Leu
                85                  90                  95

Arg Arg Leu Ser Leu Met Gly Gly Ala His Leu Thr Pro Ala Thr Pro
            100                 105                 110

Val Thr Asp Pro Arg Ala Asp His Pro Gly Leu Gln Leu Thr Gly Arg
            115                 120                 125

Ile Ile Ser Ala Ser Leu Cys Ile Pro Tyr Lys Val Ala His Gln Pro
130                 135                 140

Gly Ala Asp Trp Glu Leu Ser Pro Arg Ser Gly Thr Ser Ala Leu Phe
145                 150                 155                 160

Asp Ser Phe Ala His Leu Ala Ser Asp Arg Ser Pro Trp Asn His Thr
                165                 170                 175

Leu Val Gly Trp Thr Gly Glu Val Glu Glu Ile Val Ser Lys Arg Ala
            180                 185                 190

Pro Leu Gln Pro Val Ser Ala Asn Gly Val Pro Thr Ala Pro Leu Pro
            195                 200                 205

Val Asn Lys Ala Ser Ala Pro Val Pro Val Asp Leu Ser Gln Gln Val
210                 215                 220

Gln Ser Pro Val Asp Gly Val Leu Val Ser Ala Ala Asp Arg Glu Arg
225                 230                 235                 240

Leu Glu Arg Gln Leu Lys Ser Ser Lys Tyr Gly Arg Ile Leu Pro Val
                245                 250                 255

Trp Ala Ile Pro Glu Ser Asp Glu Pro Gln Asp Asp Ile Leu Leu Gln
            260                 265                 270

```
Asp Gln Ser Arg Trp Arg Arg Tyr Ala Glu Arg Glu Leu Tyr Pro Leu
        275                 280                 285

Leu His Tyr Lys Gln Asn Gly Pro Ser Asp Gly Arg Ser Glu Arg Lys
        290                 295                 300

Trp Trp Thr Asp Tyr Met Arg Leu Asn Arg Leu Phe Ala Asp Arg Ile
305                 310                 315                 320

Ala Gly Thr Tyr Gln Ala Gly Asp Ile Val Trp Ile His Asp Tyr His
                    325                 330                 335

Leu Phe Leu Leu Pro Asn Leu Leu Arg Gln Arg Ile Pro Asn Ile Phe
                340                 345                 350

Ile Gly Phe Phe Leu His Ser Pro Phe Pro Ser Ser Glu Tyr Met Arg
            355                 360                 365

Cys Leu Ala Lys Arg Lys Glu Val Leu Thr Gly Val Leu Gly Ala Asn
        370                 375                 380

Met Ile Gly Phe Gln Thr Tyr Ser Tyr Ser Arg His Phe Ser Ser Cys
385                 390                 395                 400

Cys Thr Arg Val Leu Gly Phe Glu Ser Asn Ser Ala Gly Val Asp Ala
                    405                 410                 415

Tyr Gly Ala His Val Ala Val Asp Val Phe Ala Thr Gly Ile Asp Ala
                420                 425                 430

Gln Asn Val Gln Arg Ala Ala Phe Gly Ser Ala Glu Thr Glu Gln Val
            435                 440                 445

Val Ala Asn Ile Lys Lys Leu Tyr Ala Gly Lys Lys Ile Ile Val Gly
        450                 455                 460

Arg Asp Arg Leu Asp Ser Val Arg Gly Val Ala Gln Lys Leu Gln Ala
465                 470                 475                 480

Phe Glu Ala Phe Leu Glu Lys Tyr Pro His Trp His Asp Lys Val Val
                    485                 490                 495

Leu Ile Gln Val Thr Ser Pro Thr Ser Met Glu Glu Gln Lys Glu Asp
                500                 505                 510

Pro Glu Asn Lys Ile Gly Ser Gln Val Ser Ser Leu Val Ser Thr Ile
            515                 520                 525

Asn Gly Arg Phe Gly Ser Leu Ser Phe Thr Pro Val Gln Tyr His Pro
        530                 535                 540

Gln Tyr Ile Ser Pro Gln Glu Tyr Phe Ser Leu Leu Arg Val Ala Asp
545                 550                 555                 560

Val Gly Leu Ile Thr Ser Val Arg Asp Gly Met Asn Thr Thr Ser Leu
                    565                 570                 575

Glu Tyr Val Leu Cys Gln Gln Gly Asn His Gly Pro Leu Ile Leu Ser
                580                 585                 590

Glu Phe Ser Gly Thr Ala Ala Met Leu Thr Ser Ala Ile His Ile Asn
            595                 600                 605

Pro Trp Asp Thr Ser Gly Val Ala Ala Ile Asp Gln Ala Leu Ser
        610                 615                 620

Met Ser Glu Lys Glu Lys Val Glu Arg His Gln Val Ala Tyr Arg His
625                 630                 635                 640

Val Thr Ser Asn Thr Val Ser Met Trp Ser Gln His Tyr Leu Asn Arg
                    645                 650                 655

Leu Leu Thr Asn Leu Ser Ser Phe Asp Gln Ser Ile Ala Thr Pro Ala
                660                 665                 670

Leu Asp Arg Ala Gln Val Leu Lys Gln Tyr Arg Lys Ala Lys Lys Arg
            675                 680                 685
```

-continued

Leu Phe Met Phe Asp Tyr Asp Gly Thr Leu Thr Pro Ile Val Lys Asp
690                 695                 700

Pro Gln Ala Ala Ile Pro Ser Asp Arg Val Leu Arg Asn Ile Lys Ser
705                 710                 715                 720

Leu Ala Ala Asp Pro Arg Asn Ser Val Trp Ile Ile Ser Gly Arg Asp
                725                 730                 735

Gln Ala Phe Leu Asp Glu Trp Met Gly His Ile Pro Glu Leu Gly Leu
            740                 745                 750

Ser Ala Glu His Gly Cys Phe Ile Arg Lys Pro Arg Ser Asp Asp Trp
        755                 760                 765

Glu Asn Leu Ala Ala Gln Ser Asp Met Ser Trp Gln Lys Asp Val Met
770                 775                 780

Asp Ile Phe Gln His Tyr Thr Glu Arg Thr Gln Gly Ser Phe Ile Glu
785                 790                 795                 800

Arg Lys Arg Val Ala Leu Thr Trp His Tyr Arg Ala Asp Pro Glu
                805                 810                 815

Tyr Gly Ala Phe Gln Ala Lys Glu Cys Arg Lys His Leu Glu Asn Thr
            820                 825                 830

Val Met Lys Lys Tyr Asp Val Glu Val Met Ala Gly Lys Ala Asn Leu
        835                 840                 845

Glu Val Arg Pro Thr Phe Val Asn Lys Gly Phe Ile Val Thr Arg Leu
850                 855                 860

Leu Asn Glu Tyr Ala Lys Gly Glu Ala Pro Glu Phe Met Phe Cys Ser
865                 870                 875                 880

Gly Asp Asp Phe Thr Asp Glu Asp Met Phe Arg Ala Leu Arg His Ser
                885                 890                 895

Asn Leu Pro Gln Glu His Ile Phe Ser Val Thr Val Gly Ala Ser Ser
            900                 905                 910

Lys Gln Thr Leu Ala Ser Trp His Leu Leu Glu Pro Ala Asp Val Ile
        915                 920                 925

Ala Thr Ile Gly Met Leu Asn Gly Thr Ser Met Gly Ala Glu Tyr Ser
930                 935                 940

<210> SEQ ID NO 8
<211> LENGTH: 33
<212> TYPE: DNA
<213> ORGANISM: Artificial Sequence
<220> FEATURE:
<223> OTHER INFORMATION: synthetic primer

<400> SEQUENCE: 8
cccctccgga gcgtgggtgg tcacgtgata ctg                                    33

<210> SEQ ID NO 9
<211> LENGTH: 33
<212> TYPE: DNA
<213> ORGANISM: Artificial Sequence
<220> FEATURE:
<223> OTHER INFORMATION: synthetic primer

<400> SEQUENCE: 9
ggcctctaga ccggagacgc acgattcaag att                                    33

<210> SEQ ID NO 10
<211> LENGTH: 23
<212> TYPE: DNA
<213> ORGANISM: Artificial Sequence
<220> FEATURE:
<223> OTHER INFORMATION: synthetic primer

<400> SEQUENCE: 10
gtcgcgatcg atggctgatt gtc                                          23

<210> SEQ ID NO 11
<211> LENGTH: 29
<212> TYPE: DNA
<213> ORGANISM: Artificial Sequence
<220> FEATURE:
<223> OTHER INFORMATION: synthetic primer

<400> SEQUENCE: 11
ttcctgacaa cgaggacatc tcaagctgt                                    29

<210> SEQ ID NO 12
<211> LENGTH: 23
<212> TYPE: DNA
<213> ORGANISM: Artificial Sequence
<220> FEATURE:
<223> OTHER INFORMATION: synthetic primer

<400> SEQUENCE: 12
tcaccggtcg gattcgccta gtt                                          23

<210> SEQ ID NO 13
<211> LENGTH: 36
<212> TYPE: DNA
<213> ORGANISM: Artificial Sequence
<220> FEATURE:
<223> OTHER INFORMATION: synthetic primer

<400> SEQUENCE: 13
ggtcagtaac atagcaggac tatagtagtg gctcac                            36

<210> SEQ ID NO 14
<211> LENGTH: 3928
<212> TYPE: DNA
<213> ORGANISM: Trichoderma reesei

<400> SEQUENCE: 14
agctcccgat agggcggcgg ccaagtcaca ggccatctca gcaaagacga ggccgagaac    60
atcaatcgac ggaaaggaga taaacgttgc gccccccag aatactagcc gtcgtcttaa   120
gccacactcc ttctcaccct tccctcctcc tgcccattct ctccctgaac ccgcacaact   180
ccaggagcag ctgtgactcc tcctgcctct cctcttctcc tgtcgtcca cacgtagcag   240 gtgctcgctg tcggtcaaca gtttgagcct ccctcagca gccggcacca agcctccgaa   300
gcgcttggca ccacagtacg aggccaagca ccgcctaacg cccttctgcc agccgctgac   360
cttgtacccc tccccctcct ccagcacagg ttcctcgaga ctttgcaagc accgaccgac   420
gtcgacaaga cacaaacaca aaaccatccg ggaacctcgc gcgcaaccgg cacaatggcg   480
cgccgtgagt ctctgtctga gattcgcgcc gccaaccccg agctcttcct gacgggcaac   540
atcatctcgg cgaccttcaa catcccccat gctgtgacat accacaaggg cggtgcttgg   600
gtgagtgcat tttcctggct gggcatcgct ttgaggacgt cctaagcttg tctgtgcttg   660
aagcacttgg cactggtcga ggcgagatca aggcagacga gctttgtttg attttctgag   720
acatctccct cctccctctg cgttgattgc ctcattctgc tgctctcctc cgtcgccccc   780
gcccgtggga agccatcatt ctgactgact ttggctgcgc aggatctgaa gccccgccgt   840
ggccagtcgg ccctcatcga ctccttcgcc tatctctcgt ccgacgcgac gcctggaat   900

```
cacacagtcg tggcctggac aggcgaaatt gccaaccccg acaacgaccc gctgtctcct    960
ccagataccc cctcagccgc ggccaccacc atcggtgctg ccaactcgct gtcggctccc   1020
gtcccgatcg atgccaccac tcggctgccc acgcctcccc cagtcgacgg gctctggatc   1080
cccaaggcag accagacgcg gctggagcac cagctgtccc acagcacaac cattcgcacc   1140
gtgcctgtct ggctggctga ccagagcgag gccaccgatg atggcatcat gctcaaggac   1200
caggctcgct ggaggcgcta tgctgagcac gatctctaca cactcttcca ctacaagcag   1260
cacgagccca cggatggccg caaggagcgg gcgcagtggg ccgactacta ccgcatgaac   1320
cagaagttcg ccaacaagat cattgagatc tacaagcctg gtgacgttgt catcgttcat   1380
gattactatc tgatgctgct gcccagcatg ctccgccagc gggctcccaa gatgtacatc   1440
tccttcttcc tccactcgcc cttccccagc agcgagttcc tccgttgcct gccccgccgc   1500
aaggaggtgc ttgagggtgt cctgggcgcc aatctcgtgg gcttccagtc ttacagctac   1560
tcgcgccact cctcagctg ctgcacccgc atcctcggtt tcccctctga cactcttggc   1620
atcgacgcct atggctccag ggtgcaggtc ggagtgtttc ccattggcat cgacgccgcc   1680
aaggtggaga ccgccgcctg gcggacaccc gtcaacgaga agcacgctgc cgtcctgaag   1740
atgtacgaag gcaagaagat catcgtcggc cgagatcgtt tggacagcgt gaggggcgtt   1800
gctcaaaagc tgcaggcgtt tgagcgcttc ctggagctgt accctcactg gcgcgagaag   1860
gtggtcctga tccaggtcac gtcgccacc agcatcgagg ctgagaaggg tgacccggag   1920
aacaagaacg ccagtcgagt caacgagctc atcaccaaga tcaatggcga atacggcagt   1980
ctcggctttt cgcctgtgca gcactacccc cagtacctca gccaggccga gtactttgcc   2040
ttgctccggg ccgcagacat tggcctcatc acctcggtgc gagatggaat gaacacgaca   2100
agtctcgagt acgttgtctg ccagaaggat agcaacggcc cactcattct ctccgagttc   2160
agcggcaccg cgggtagtct ccgcgacgcc atccacatca ccccctggga tctgacgggc   2220
gtggcggaaa agatcaacgc ggctctggag atgtctgagg aggagcgcgt caagatgcag   2280
acaagcctct acacccacgt cacgacgcag aatgtccagt cgtggatcac caagttcatc   2340
cgcaagttcc acgcggcgct gagcgagacc aactcagtca catcgacacc ccttctcgac   2400
cgcgcgctct tgctgtcccg ttaccgcgcc gccaagaagc gcctgttcat gtttgactac   2460
gacggcaccc tcacgcccat tgtgcgcgaa ccgagcgccg ctgttccttc ggagcgcatc   2520
atccgctacc tgcagtcgct tgcatcggac cccaggaacg cggtctggat catctctggc   2580
cgagaccaag agttccttca gcaacatctc ggccacatcc cccggatcgg attctctgcc   2640
gagcatggta gtttcatgcg agaccccggc agcgacgagt gggttaacct ggcagagaag   2700
tttgacatgg gctggcaggc agaggtcatg gaggtgttcc agcgttacac ggacaaggtt   2760
ccaggtgagt tgctgtctat cccgagtttg agttgcctca agaacaatc ctatcacggg   2820 ttaaggcaag acaagacaga aagcagaagc taacacacta tccttaggtt ccttcatcga   2880
gcgaaaacgc tgcgccctga cctggcatta tcgactggcc gagccggagc aaggcctcca   2940
catgtcacgc gagtgtcacc gagagctcga accggcatt gcccagcgat gggaggtcga   3000
ggtgatgcct ggcaaggcca acatcgaggt gcgccctacg ttcatcaaca agggtgagat   3060
cgccaagcga ctggtggcca cttatcacaa cccgggagcc gccccgaccg acaaggaccc   3120
ttaccccgga aagattgagt ttgctctctg ctctggagac gactttaccg acgaggacat   3180
gttccgcagc ctcaacggag catgtggcac gatcctggaa gaccagcacg tcttcaccgt   3240
cactgtggga gccagcacca aggtgacgct ggccaaatgg catctcctgg agcccgagga   3300
```

```
cgtgattgag tgcgtgggtc tgctggctgg tgctggcgac ccggccagcc tcgagcgtgt    3360
tggagaggtg aacctggccg ctttgagcca ggtggagggt cacattcccg ccgaggagct    3420
gtaaaggaca ttcgtttgtc ccagtgcttt caggcgtgga atggcctctt gatgggaaac    3480
cacgaggctt tctccagatg ctgaacttga gtgtttggca aagtctgggg gtgattcttt    3540
tccttttgac gacttgcaca tttgagatga agagagcgaa aacggacgca tagaacggta    3600
atagaaacga aggatggcgc gtggcgtacg ggctagtaat gaccttgtgg cacagaatct    3660
gtgataaaga gtaaaaaaaa aggaaacaaa ggccccccg agagacagaa aaatatcaaa     3720
agaagaagaa aaaaaaaaaa aaaatcacgg cagcaaatac gggacaaaaa ggggattgcg    3780
gacgctctgg taatctgaca tggaaagttc cgcgatgaac tggcaaagta tacagagtag    3840
catcagtcgc gattcattta gcgtggagaa taagacaaag tttaacctcg acttgtgttg    3900
cactgcagct gagtttcaat cttgaatc                                      3928
```

FILAMENTOUS FUNGI HAVING AN ALTERED VISCOSITY PHENOTYPE

PRIORITY CROSS REFERENCE TO RELATED APPLICATIONS

The present application is a 371 National Stage application of PCT/US2012/034409, filed on Apr. 20, 2012, which claims priority to U.S. Provisional Application Ser. Nos. 61/478,162, and 61/478,160, both filed on Apr. 22, 2011 and 61/480,610, 61/480,602 and 61/480,629, each filed on Apr. 29, 2011, which are hereby incorporated by reference in their entirety.

SEQUENCE LISTING

The sequence listing submitted via EFS, in compliance with 37 C.F.R. §1.52(e), is incorporated herein by reference. The sequence listing text file submitted via EFS contains the file "40012WO_ST25.txt" created on Oct. 24, 2013, which is 61,440 bytes in size.

TECHNICAL FIELD

The present strains and methods relate to genetic mutations in filamentous fungi that give rise to strain variants having altered growth characteristics. Such variants are well-suited for growth in submerged cultures, e.g., for the large-scale production of enzymes and other proteins or metabolites for commercial applications.

BACKGROUND

Filamentous fungi are capable of expressing native and heterologous proteins to high levels, making them well-suited for the large-scale production of enzymes and other proteins for industrial, pharmaceutical, animal health and food and beverage applications. Filamentous fungi are typically grown in mycelial submerged cultures in bioreactors, which are adapted to introduce and distribute oxygen and nutrients into the culture medium (i.e., broth). The morphological characteristics of the mycelium affect the rheological properties of the broth, thereby affecting bioreactor performance.

Generally, the higher the viscosity of the broth, the less uniform the distribution of oxygen and nutrients, and the more energy required to agitate the culture. In some cases, the viscosity of the broth becomes sufficiently high to significantly interfere with the dissolution of oxygen and nutrients, thereby adversely affecting the growth of the fungi. Additionally, the power required to mix and aerate viscous broth can significantly increase the cost of production, and incur higher capital expenditures in terms of motors and power supplies.

SUMMARY

Described are strains and methods relating to filamentous fungi having genetic alterations that give rise to altered viscosity phenotypes.

In one aspect, a variant strain of filamentous fungus derived from a parental strain is provided, the variant strain comprising a genetic alteration that causes cells of the variant strain to produce an altered amount of functional Tps2 protein compared to cells of the parental strain, wherein the cells of the variant strain are produced during aerobic fermentation in submerged culture cell broth that (i) requires an altered amount of agitation to maintain a preselected dissolved oxygen content compared to the cells of the parental strain, and/or (ii) maintains an altered dissolved oxygen content at a preselected amount of agitation, compared to the cells of the parental strain.

In some embodiments, the altered amount of functional Tps2 protein is a reduced amount, and the variant strain produces during aerobic fermentation in submerged culture a cell broth that (i) requires reduced agitation to maintain a preselected dissolved oxygen content compared to the cells of the parental strain, and/or (ii) maintains an increased dissolved oxygen content at a preselected amount of agitation, compared to the cells of the parental strain.

In some embodiments, the genetic alteration comprises a disruption of the tps2 gene present in the parental strain. In some embodiments, disruption of the tps2 gene is the result of deletion of all or part of the tps2 gene. In some embodiments, disruption of the tps2 gene is the result of deletion of a portion of genomic DNA comprising the tps2 gene. In some embodiments, disruption of the tps2 gene is the result of mutagenesis of the tps2 gene.

In some embodiments, disruption of the tps2 gene is performed using site-specific recombination. In some embodiments, disruption of the tps2 gene is performed in combination with introducing a selectable marker at the genetic locus of the tps2 gene.

In some embodiments, the variant strain does not produce functional Tps2 protein. In some embodiments, the variant strain does not produce Tps2 protein.

In some embodiments, the variant strain further comprises a gene encoding a protein of interest. In some embodiments, the variant strain further comprises a disruption of the sfb3 gene. In some embodiments, the variant strain further comprises a disruption of the seb1 gene. In some embodiments, the variant strain further comprises a disruption of the sfb3 and seb1 genes. In some embodiments, the variant strain further comprises a disruption of at least one gene selected from the group consisting of the sfb3 gene, the seb1 gene, the mpg1 gene, the gas1 gene, and the crz1 gene. In some embodiments, the variant strain produces substantially the same amount of, or more, protein per unit amount of biomass as the parental strain.

In some embodiments, the filamentous fungus is a Pezizomycotina species. In some embodiments, the filamentous fungus is a *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., and *Neurospora* spp. In some embodiments, the filamentous fungus can include, but is not limited to, *Trichoderma reesei* (previously classified as *Trichoderma longibrachiatum* and *Hypocrea jecorina*), *Aspergillus niger, Aspergillus fumigatus, Aspergillus itaconicus, Aspergillus oryzae, Aspergillus nidulans, Aspergillus terreus, Aspergillus sojae, Aspergillus japonicus, Scedosporium prolificans, Neurospora crassa, Penicillium funiculosum, Penicillium chrysogenum, Talaromyces (Geosmithia) emersonii, Fusarium venenatum*, and *Chrysosporium lucknowense*. In some embodiments, the filamentous fungus is *Trichoderma reesei*.

In another aspect, a method for producing a variant strain of filamentous fungus cells is provided, comprising: introducing a genetic alteration into a parental strain of filamentous fungal cell, which genetic alteration alters the production of functional Tps2 protein compared to the cells of the parental strain, thereby producing a variant filamentous fungal cell that produces during aerobic fermentation in submerged culture a cell broth that (i) requires an altered amount of agitation to maintain a preselected dissolved oxygen content, compared to the cells of the parental strain, and/or (ii) maintains an altered dissolved oxygen content at a preselected amount of agitation, compared to the cells of the parental strain.

In some embodiments, the genetic alteration reduces or prevents the production of functional Tps2 protein, thereby producing a variant filamentous fungal cell that produces during aerobic fermentation in submerged culture a cell broth that (i) requires reduced agitation to maintain a preselected dissolved oxygen content, compared to the cells of the parental strain, and/or (ii) maintains an increased dissolved oxygen content at a preselected amount of agitation, compared to the cells of the parental strain.

In some embodiments, the genetic alteration comprises disrupting the tps2 gene in a parental filamentous fungal cell using genetic manipulation. In some embodiments, the genetic alteration comprises deleting the tps2 gene in a parental filamentous fungal cell using genetic manipulation. In some embodiments, the genetic alteration is performed using site-specific genetic recombination.

In some embodiments, disruption of the tps2 gene is performed in combination with introducing a selectable marker at the genetic locus of the tps2 gene. In some embodiments, the variant strain produces substantially the same amount of, or more, protein per unit amount of biomass as the parental strain. In some embodiments, disruption of the tps2 gene is performed in combination with disrupting the sfb3 gene. In some embodiments, disruption of the tps2 gene is performed in combination with disrupting at least one gene selected from the group consisting of the sfb3 gene, the seb1 gene, the mpg1 gene, the gas1 gene, and the crz1 gene.

In some embodiments, the variant strain produces substantially the same amount of, or more, protein per unit amount of biomass as the parental strain.

In some embodiments, the filamentous fungus is a Pezizomycotina species. In some embodiments, the filamentous fungus is a *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., and *Neurospora* spp. In some embodiments, the filamentous fungus can include, but is not limited to, *Trichoderma reesei* (previously classified as *Trichoderma longibrachiatum* and *Hypocrea jecorina*), *Aspergillus niger*, *Aspergillus fumigatus*, *Aspergillus itaconicus*, *Aspergillus oryzae*, *Aspergillus nidulans*, *Aspergillus terreus*, *Aspergillus sojae*, *Aspergillus japonicus*, *Scedosporium prolificans*, *Neurospora crassa*, *Penicillium funiculosum*, *Penicillium chrysogenum*, *Talaromyces* (*Geosmithia*) *emersonii*, *Fusarium venenatum*, and *Chrysosporium lucknowense*. In some embodiments, the filamentous fungus is *Trichoderma reesei*.

In some embodiments, the parental strain further comprises a gene encoding a protein of interest. In some embodiments, the gene encoding the protein of interest is present in the parental strain prior to introducing the genetic alteration that reduces or prevents the production of functional Tps2 protein. In some embodiments the protein of interest within the parental strain is encoded by an endogenous gene or a heterologous gene.

In another aspect, a protein of interest produced by any of the aforementioned variant strains is provided.

In yet another aspect, a filamentous fungus produced by any of the aforementioned methods and having any of the aforementioned properties is provided.

In another aspect, a variant strain of filamentous fungus derived from a parental strain is provided, the variant strain comprising: (a) a genetic alteration that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, and (b) a gene encoding a protein of interest, wherein the gene encoding the protein of interest is present in the variant strain prior to the genetic alteration in (a).

In some embodiments, the genetic alteration of the resulting variant strain comprises a disruption of the tps2 gene present in the parental strain. In some embodiments, disruption of the tps2 gene is performed in combination with introducing a selectable marker at the genetic locus of the tps2 gene. In some embodiments, disruption of the tps2 gene is performed in combination with disrupting the sfb3 gene. In some embodiments, disruption of the tps2 gene is performed in combination with disrupting the seb1 gene. In some embodiments, disruption of the tps2 gene is performed in combination with disrupting at least one gene selected from the group consisting of the sfb3 gene, the seb1 gene, the mpg1 gene, the gas1 gene, and the crz1 gene.

These and other aspects and embodiments of present variant strains and methods will be apparent from the description, including the accompanying FIGURE.

BRIEF DESCRIPTION OF THE DRAWING

FIG. 1 is a map of the tps2 disruption vector, pRATT251-tps2D-pyr2, as described in Example 1.

DETAILED DESCRIPTION

I. Overview

The present strains and methods relate to variant strains of filamentous fungus cells having genetic modifications that affect their morphology and growth characteristics. When the variant cells are grown in submerged culture, they produce a cell broth that has different rheological properties compared to a cell broth comprising cells of the parental strain. Some of these variant strains are well-suited for the large-scale production of enzymes and other commercially important proteins.

II. Definitions

Prior to describing the present strains and methods in detail, the following terms are defined for clarity. Terms not defined should be accorded their ordinary meanings as used in the relevant art.

As used herein, "*Trichoderma reesei*" refers to a filamentous fungus of the phylum Ascomycota, subphylum Pezizomycotina. This organism was previously classified as *Trichoderma longibrachiatum*, or as *Hypocrea jecorina*.

As used herein, the phrase "variant strain of filamentous fungus cells," or similar phrases, refer to strains of filamentous fungus cells that are derived (i.e., obtained from or obtainable from) from a parental (or reference) strain belonging to the Pezizomycotina, e.g., by genetic manipulation. In the present description, parental and variant strains can be described as having certain characteristics, such as genetic modifications, expression phenotypes, morphology, and the like; however, the skilled person will appreciate that it is technically the cells of the parental or variant strain that have such characteristics, and "the strains" are referred to for convenience.

As used herein, the term "protein of interest" refers to a polypeptide that is desired to be expressed in a filamentous fungus. Such a protein can be an enzyme, a substrate-binding protein, a surface-active protein, a structural protein, or the like, and can be expressed at high levels, and can be for the purpose of commercialization. The protein of interest can be encoded by an endogenous gene or a heterologous gene relative to the variant strain and/or the parental strain. The protein of interest can be expressed intracellularly or as a secreted protein.

As used herein, the phrase "substantially free of an activity," or similar phrases, means that a specified activity is either undetectable in an admixture or present in an amount that would not interfere with the intended purpose of the admixture.

As used herein, the terms "polypeptide" and "protein" (and/or their respective plural forms) are used interchangeably to refer to polymers of any length comprising amino acid residues linked by peptide bonds. The conventional one-letter or three-letter codes for amino acid residues are used herein. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are deemed "related proteins." Such proteins can be derived from organisms of different genera and/or species, or even different classes of organisms (e.g., bacteria and fungi). Related proteins also encompass homologs determined by primary sequence analysis, determined by secondary or tertiary structure analysis, or determined by immunological cross-reactivity.

As used herein, the term "derivative polypeptide/protein" refers to a protein, which is derived or derivable from a protein by addition of one or more amino acids to either or both the N- and C-terminal end(s), substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. The preparation of a protein derivative can be achieved by modifying a DNA sequence, which encodes for the native protein, transformation of that DNA sequence into a suitable host, and expression of the modified DNA sequence to form the derivative protein.

Related (and derivative) proteins include "variant proteins." Variant proteins differ from a reference/parental protein (e.g., a wild-type protein) by substitutions, deletions, and/or insertions at a small number of amino acid residues. The number of differing amino acid residues between the variant and parental protein can be one or more, for example, 1, 2, 3, 4, 5, 6, 7, 8, 9, 10, 15, 20, 30, 40, 50, or more amino acid residues. Variant proteins can share at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with a reference protein. A variant protein can also differ from a reference protein in selected motifs, domains, epitopes, conserved regions, and the like.

As used herein, the term "analogous sequence" refers to a sequence within a protein that provides similar function, tertiary structure, and/or conserved residues as the protein of interest (i.e., typically the original protein of interest). For example, in epitope regions that contain an α-helix or a β-sheet structure, the replacement amino acids in the analogous sequence preferably maintain the same specific structure. The term also refers to nucleotide sequences, as well as amino acid sequences. In some embodiments, analogous sequences are developed such that the replacement amino acids result in a variant enzyme showing a similar or improved function. In some embodiments, the tertiary structure and/or conserved residues of the amino acids in the protein of interest are located at or near the segment or fragment of interest. Thus, where the segment or fragment of interest contains, for example, an α-helix or a β-sheet structure, the replacement amino acids preferably maintain that specific structure.

As used herein, the term "homologous protein" refers to a protein that has similar activity and/or structure to a reference protein. Homologs are not necessarily evolutionarily related. Thus, it is intended that the term encompasses the same, similar, or corresponding enzyme(s) (e.g., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman (1981) *Adv. Appl. Math.* 2:482; Needleman and Wunsch (1970) *J. Mol. Biol.*, 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, Wis.); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989)

Proc. Natl. Acad. Sci. USA 89:10915) alignments (B) of 50, expectation (E) of 10, M'5, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (e.g., wild-type) sequence. Sequence identity can be determined using known programs such as BLAST, ALIGN, and CLUSTAL using standard parameters. (See, e.g., Altschul, et al. (1990) *J. Mol. Biol.* 215:403-410; Henikoff et al. (1989) *Proc. Natl. Acad. Sci. USA* 89:10915; Karin et al. (1993) *Proc. Natl. Acad. Sci USA* 90:5873; and Higgins et al. (1988) *Gene* 73:237-244). Software for performing BLAST analyses is publicly available through the National Center for Biotechnology Information. Also, databases can be searched using FASTA (Pearson et al. (1988) *Proc. Natl. Acad. Sci. USA* 85:2444-48). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, the terms "wild-type" and "native" are used interchangeably and refer to genes, proteins, or strains found in nature.

As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences.

As used herein, "disruption of a gene" refers broadly to any genetic or chemical manipulation, i.e., mutation, that substantially prevents a cell from producing a function gene product, e.g., a protein, in a host cell. Examples of methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using RNAi, antisense, or any other method that abolishes gene expression.

As used herein, the terms "genetic manipulation" and "genetic alteration" are used interchangeably and refer to the alteration/change of a nucleic acid sequence. The alteration can included but is not limited to a substitution, deletion, insertion or chemical modification of at least one nucleic acid in the nucleic acid sequence.

As used herein, "aerobic fermentation" refers to growth in the presence of oxygen.

As used herein, the term "cell broth" refers collectively to medium and cells in a liquid/submerged culture.

As used herein, the term "cell mass" refers to the cell component (including intact and lysed cells) present in a liquid/submerged culture. Cell mass can be expressed in dry or wet weight.

As used herein, the term "rheology" refers to a branch of physics dealing with the deformation and flow of matter.

As used herein, "viscosity" is a measure of the resistance of a fluid to deformation by mechanical stress, such as shear stress or tensile stress. In the present context, viscosity can also refer to the resistance of a cell broth comprising filamentous fungus cells to mechanical stress, e.g., as provided by a rotor/impeller. Because the viscosity of a cell broth can be difficult to measure directly, indirect measurements of viscosity can be used, such as the dissolved oxygen content of the culture broth at a preselected amount of agitation, the amount of agitation required to maintain a preselected dissolved oxygen content, the amount of power required to agitate a cell broth to maintain a preselected dissolved oxygen content, or even colony morphology on solid medium.

As used herein, an "altered-viscosity" variant strain of filamentous fungus cells refers to a variant strain that produces a cell broth that has a reduced or increased viscosity (i.e., reduced or increased resistance to shear or tensile stress) compared to an equivalent cell broth produced by a parental strain. Generally, comparable cell broths or equivalent cell broths have comparable cell masses. Preferably, the difference between a variant, altered viscosity strain and a parental strain, with respect to any direct or indirect measure of viscosity, is at least 10%, at least 15%, at least 20%, at least 25%, at least 30%, at least 35%, at least 40%, at least 45%, or even at least 50%, or more. Methods for comparing the viscosity of filamentous fungus cells broth are described herein.

As used herein, a "reduced-viscosity" variant strain of filamentous fungus cells refers to a variant strain that produces a cell broth that has reduced viscosity (i.e., reduced resistance to shear or tensile stress) compared to an equivalent cell broth produced by a parental strain. Preferably, the difference between a variant, altered viscosity strain and a parental strain, with respect to any direct or indirect measure of viscosity, is at least 10%, at least 15%, at least 20%, at least 25%, at least 30%, at least 35%, at least 40%, at least 45%, or even at least 50%, or more.

As used herein, "dissolved oxygen" (DO) refers to the amount of oxygen ($O_2$) present in a liquid medium as measured in vol/vol units. The dissolved oxygen level can be maintained at a high level, e.g., between 170-100% and 20%, between 100-80% and 20%, between 70% and 20%, between 65% and 20%, between 60% and 20%, between 55% and 20%, between 50% and 20%, between 45% and 20%, between 44% and 20%, between 43% and 20%, between 42% and 20%, between 41% and 20%, between 40% and 20%, between 35% and 20%, between 30% and 20%, and between 25% and 20% throughout the fermentation. In particular, the dissolved oxygen can be high at the beginning of the fermentation and to be permitted to fall as the fermentation progresses. The dissolved oxygen level can be controlled by the rate at which the fermentation is agitated, e.g. stirred, and/or by the rate of addition of air or oxygen. The culture can be agitated, e.g., stirred at between 400-700 rpm and the dissolved oxygen level is maintained above 20%, above 25%, above 30%, above 35%, above 40%, above 45%, above 50% and above 55% or more by altering the air or oxygen flow rate and impeller speed.

As used herein, a "primarily genetic determinant" refers to a gene, or genetic manipulation thereof, that is necessary and sufficient to confer a specified phenotype in the absence of other genes, or genetic manipulations, thereof. However, that a particular gene is necessary and sufficient to confer a specified phenotype does not exclude the possibility that additional effects to the phenotype can be achieved by further genetic manipulations.

As used herein, a "functional polypeptide/protein" is a protein that possesses an activity, such as an enzymatic activity, a binding activity, a surface-active property, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, variant cells "maintain or retain a high level of protein expression and/or secretion" compared to a parental strain if the difference in protein expression between the variant strain and a parental strain is less than about 20%, less than about 15%, less than about 10%, less than about 7%, less than about 5%, or even less than about 3%.

As used herein, host cells have been "modified to prevent the production of a specified protein" if they have been genetically or chemically altered to prevent the production of a functional protein/polypeptide that exhibits an activity characteristic of the wild-type protein, particularly an activity that promotes elongation of hyphae or otherwise increases the viscosity of a filamentous fungus in liquid culture. Such modifications include, but are not limited to, deletion or disruption of the gene encoding the protein, modification of the gene such that the encoded polypeptide lacks the aforementioned activity, modification of the gene to affect post-translational processing or stability, and combinations, thereof.

As used herein, a "protein of interest" is a protein that is desired to be produced in a submerged culture of filamentous fungus cells. Generally, proteins of interest are commercially important for industrial, pharmaceutical, animal health, and food and beverage use, making them desirable to produce in large quantities. Proteins of interest are to be distinguished from the myriad other proteins expressed by the filamentous fungus cells, which are generally not of interest as products and are mainly considered background protein contaminants.

As used herein, a variant strain produces "substantially the same amount" of protein per unit amount of biomass as a parental strain if the amount of protein produced by the variant strain is no more than 20% reduced, no more than 15% reduced, no more than 10% reduced, an even no more than 5% reduced compared to the amount of protein produced by the parental strain, wherein the amount of protein is normalized to the total amount of biomass of cells from which protein production is measured, wherein biomass can be expressed in terms of either wet (e.g., of cell pellet) or dry weight.

As used herein, a variant strain produces "substantially more protein per unit amount of biomass" than a parental strain if the amount of protein produced by the variant strain is at least 5% increased, at least 10% increased, at least 15% increased, or more, compared to the parental strain, wherein the amount of protein is normalized to the total amount of biomass of cells from which protein production is measured, wherein biomass can be expressed in terms of either wet (e.g., of cell pellet) or dry weight.

As used herein, "fluorochromes" are fluorescent dyes. Preferred fluorochromes bind to cellulose and/or chitin in the cell walls of fungi.

As used herein, the singular articles "a," "an," and "the" encompass the plural referents unless the context clearly dictates otherwise. All references cited herein are hereby incorporated by reference in their entirety. The following abbreviations/acronyms have the following meanings unless otherwise specified:

CFU colony forming units
EC enzyme commission
kDa kiloDalton
kb kilobase
MW molecular weight
w/v weight/volume
w/w weight/weight
v/v volume/volume
wt % weight percent
° C. degrees Centigrade
$H_2O$ water
$H_2O_2$ hydrogen peroxide
$dH_2O$ or DI deionized water
$dIH_2O$ deionized water, Milli-Q filtration
DO dissolved oxygen
g or gm gram
μg microgram
mg milligram
kg kilogram
lb pound
μL and μl microliter
mL and ml milliliter
mm millimeter
μm micrometer
mol mole
mmol millimole
M molar
mM millimolar
μM micromolar
nm nanometer
U unit
ppm parts per million
sec and " second
min and ' minute
hr and h hour
EtOH ethanol
eq. equivalent
N normal
PCR polymerase chain reaction
DNA deoxyribonucleic acid
FOA fluoroorotic acid
UV ultraviolet
$A_{540}$ absorbance measured at a wavelength of 540 nm
CMC carboxymethyl cellulose
rpm revolutions per minute Δ relating to a deletion
CER CO$_2$ evolution rate
bp base pairs

III. Filamentous Fungal Strain with Altered Tps2 Protein Production

In one aspect, a variant strain of filamentous fungus derived from a parental strain is provided, the variant strain comprising a genetic alteration that causes cells of the variant strain to produce an altered amount of functional Tps2 protein compared to cells of the parental strain. The cells of the variant strain subsequently produce, during aerobic fermentation in submerged culture, a cell broth that requires an altered amount of agitation to maintain a preselected dissolved oxygen content, or a cell mass that maintains an altered dissolved oxygen content at a preselected amount of agitation, compared to the cells of the parental strain.

In some cases, the genetic alteration causes cells of the variant strain to produce a reduced amount of functional Tps2 protein compared to cells of the parental strain, and the resulting cell broth requires reduced agitation to maintain a preselected dissolved oxygen content, or maintains a higher dissolved oxygen content at a preselected amount of agitation, compared to the cells of the parental strain. In such cases, it is believed that the cell mass of the variant strain exhibits reduced viscosity compared to the cell mass of the parental strain, which accounts for the observations relating to dissolved oxygen content and agitation as described in the Examples.

The reduction in the amount of functional Tps2 protein can result from disruption of the tps2 gene present in the parental strain. Because disruption of the tps2 gene is a primary genetic determinant for conferring a reduced viscosity phenotype to the variant strain, such variant strains need only comprise a disrupted tps2 gene, while all other genes can remain intact. In some cases, the variant strains can optionally include additional genetic alterations compared to the parental stain from which they are derived. Such additional genetic alterations are not necessary to confer a reduction in viscosity but can further reduce viscosity or confer other advantages for the variant strain.

Disruption of the tps2 gene can be performed using any suitable methods that substantially prevent expression of a function tps2 gene product, i.e., the Tps2 protein. Exemplary methods of disruption as are known to one of skill in the art include but are not limited to: Complete or partial deletion of the tps2 gene, including complete or partial deletion of, e.g., the Tps2-coding sequence, the promoter, the terminator, an enhancer, or another regulatory element. Disruption of the tps2 gene can also be performed by the complete or partial deletion of a portion of the chromosome that includes any portion of the tps2 gene. Particular methods of disrupting the tps2 gene include making nucleotide substitutions or insertions in any portion of the tps2 gene, e.g., the Tps2-coding sequence, the promoter, the terminator, an enhancer, or another regulatory element. Preferably, deletions, insertions, and/or substitutions (collectively referred to as mutations) are made by genetic manipulation using sequence-specific molecular biology techniques, as opposed to by chemical mutagenesis, which is generally not targeted to specific nucleic acid sequences. Nonetheless, chemical mutagenesis can be used to disrupt the tps2 gene.

Mutations in the tps2 gene can reduce the efficiency of the tps2 promoter, reduce the efficiency of a tps2 enhancer, interfere with the splicing or editing of the tps2 mRNA, interfere with the translation of the tps2 mRNA, introduce a stop codon into the Tps2-coding sequence to prevent the translation of full-length Tps2 protein, change the coding sequence of the Tps2 protein to produce a less active or inactive protein or reduce Tps2 interaction with other nuclear protein components, change the coding sequence of the Tps2 protein to produce a less stable protein or target the protein for destruction, cause the Tps2 protein to misfold or be incorrectly modified (e.g., by glycosylation), or interfere with cellular trafficking of the Tps2 protein.

In one embodiment, these and other genetic manipulations is to reduce or prevent the expression of a functional Tps2 protein, or reduce or prevent the normal biological activity of the Tps2 protein, thereby producing a morphology change that results in a reduced viscosity phenotype.

In other cases, the genetic alteration increases or restores the expression of a functional Tps2 protein, or increases the normal biological activity of the Tps2 protein, thereby producing a morphology change that results in an increased or restored viscosity phenotype. Exemplary genetic alterations that increase or restore Tps2 function are those that introduce addition copies of the tps2 gene into a cell, increase the efficiency of the tps2 promoter, enhancer, or other control element, increase the translation of the mRNA encoding the Tps2 protein, increase the stability of mRNA encoding the Tps2 protein, introduce changes in the tps2 gene that increase the activity or stability of the Tps2 protein, introduce changes in the tps2 gene that modulate the interaction with other proteins or nucleic acids and the like. Other genetic alterations that increase or restore Tps2 function are those that reverse the effect of genetic alterations, which reduce or prevent the expression of a functional Tps2 protein.

Filamentous fungus cells for manipulation and use as described are generally from the phylum Ascomycota, subphylum Pezizomycotina, particularly fungi that have a vegetative hyphae state and include a homolog of the tps2 gene. Such organisms include filamentous fungus cells used for the production of commercially important industrial and pharmaceutical proteins, including, but are not limited to *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., and *Neurospora* spp. Particular organisms include, but are not limited to, *Trichoderma reesei* (previously classified as *Trichoderma longibrachiatum* or *Hypocrea jecorina*), *Aspergillus niger*, *Aspergillus fumigatus*, *Aspergillus itaconicus*, *Aspergillus oryzae*, *Aspergillus nidulans*, *Aspergillus terreus*, *Aspergillus sojae*, *Aspergillus japonicus*, *Scedosporium prolificans*, *Neurospora crassa*, *Penicillium funiculosum*, *Penicillium chrysogenum*, *Talaromyces* (*Geosmithia*) *emersonii*, *Fusarium venenatum*, and *Chrysosporium lucknowense*.

The gene tps2 encodes a trehalose-phosphate phosphatase involved in the synthesis of the disaccharide trehalose. Trehalose is a stress induced sugar that buffers the refolding of denatured proteins in the cytoplasm and ER (Singer et al. 1998, Simola, et al. 2000). This disaccharide is produced in large quantities by diverse organisms in response to a variety of stresses. In yeast, trehalose stabilizes proteins at high temperatures and assists in refolding heat damaged proteins (Simola, M et al. 2000).

A disruption in the tps2 homologue orlA in *A. nidulans* results in reduced chitin and increased sensitivity to high temperature (Borgia, P. et al. 1996). Disruption of orlA in *A. fumigatus* results in increased sensitivity to calcofluor white and Congo red. Based on these results, and not wishing to be bound to a theory, it is believed that the alteration of tps2 expression and/or activity in filamentous fungi can alter the cell wall, thereby producing a more compact cellular morphology characterized by shorter hyphae and/or a more yeast-like appearance. The present disclosure provides experimental evidence of the association of Tps1 with altered morphology.

Using BLAST to search publicly available genome sequences of filamentous fungi and yeast using the *T. reesei* Tps2 amino acid sequence as query, homologs were found, although the function of these proteins was heretofore unknown. The amino acid sequences of the *T. reesei* (SEQ ID NO:1), *B. bassiana* (SEQ ID NO:2), *S. cerevisiae* S288c (SEQ ID NO:3), *A. flavus* NRRL 3357 (SEQ ID NO:4), *A. oryzae* (SEQ ID NO:5), *A. clavatus* (SEQ ID NO:6), and *T. stipitatus* ATCC 10500 (SEQ ID NO:7) Tps2 proteins are shown below.

The predicted amino acid sequence of the *Trichoderma reesei* Tps2 protein is shown below as SEQ ID NO: 1:

MARRESLSEIRAANPELFLTGNIISATFNIPHAVTYHKGGAWDLKPRRG

QSALIDSFAYLSSDATPWNHTVVAWTGEIANPDNDPLSPPDTPSAAATT

IGAANSLSAPVPIDATTRLPTPPPVDGLWIPKADQTRLEHQLSHSTTIR

TVPVWLADQSEATDDGIMLKDQARWRRYAEHDLYTLFHYKQHEPTDGRK

ERAQWADYYRMNQKFANKIIEIYKPGDVVIVHDYYLMLLPSMLRQRAPK

MYISFFLHSPFPSSEFLRCLPRRKEVLEGVLGANLVGFQSYSYSRHFLS

CCTRILGFPSDTLGIDAYGSRVQVGVFPIGIDAAKVETAAWADTVNEKH

AAVLKMYEGKKIIVGRDRLDSVRGVAQKLQAFERFLELYPHWREKVVLI

QVTSPTSIEAEKGDPENKNASRVNELITKINGEYGSLGFSPVQHYPQYL

SQAEYFALLRAADIGLITSVRDGMNTTSLEYVVCQKDSNGPLILSEFSG

TAGSLRDAIHINPWDLTGVAEKINAALEMSEEERVKMQTSLYTHVTTQN

VQSWITKFIRKFHAALSETNSVTSTPLLDRALLLSRYRAAKKRLFMFDY

DGTLTPIVREPSAAVPSERIIRYLQSLASDPRNAVWIISGRDQEFLQQH

LGHIPRIGFSAEHGSFMRDPGSDEWVNLAEKFDMGWQAEVMEVFQRYTD

KVPGSFIERKRCALTWHYRLAEPEQGLHMSRECHRELETGIAQRWEVEV

MPGKANIEVRPTFINKGEIAKRLVATYHNPGAAPTDKDPYPGKIEFALC

SGDDFTDEDMFRSLNGACGTILEDQHVFTVTVGASTKVTLAKWHLLEPE

DVIECVGLLAGAGDPASLERVGEVNLAALSQVEGHIPAEEL

The amino acid sequence of the *B. bassiana* Tps2 protein is shown below as SEQ ID NO: 2:

MARRESLSEILAANPELSLSGSIISAAFNIPHALTYRKGGDWGLKPRGG

QSALFDSFAYLSSSANPFKHTVVSWTGEIDSPQGPLEPEPQRPRSTTVG

VSSLNPLSAPIPVDGIVQLPTPPSSDGLWLPKADQERLEHQLSNDKTIR

TVPVWLADEDEITPDGIMLRDQGRWRGYAHRDLYSLFHYKQHEPSDGRK

EKIEWADYYRMNQKFAAKILEIYKPGDIVIIHDYFLMLLPSMLRQAVPN

MYISFYLHCPFPSSEFLRCLPRRREVLEGILGSNLVGFQSYSYSRHFLS

CCTRILGFPSDTLGVDAYGSRVQVGVFPIGIDAAKVEKLAWASSVDEKY

DALKKMYAGKKIIVGRDRLDSVRGVVQKLQAFDRFLEMYSEWREKVVLI

QVTSPTNKVADKEDGEHKTSTRVNELVMQINGKYGSLGFSPVQHYPQYI

NQDEYFALLRAADIGLITSVRDGMNTTSLEYVVCQKDGHGPLILSEFSG

TAASLSDAIHINPWDLTDVAGKINGALTMPDDARSKMQSRLYEHVTTQT

VQSWITKFIRRIHSVLGDKSIQHSTPLLDRALLLSQYRAASKRIFMFDY

DGTLTPIVREPSAAVPSEKLLESLKILAAEPRNSVWIISGRDQEFLTQH

LGHIPELGFSAEHGSFMRDPGSQEWINLADKFDMGWQNEVIDVFQKYTD

KVTGSFIERKRCAITWHYRLADPEQGLHMSRVAHKEVEETVAKKWDVEV

MAGKANIEVRPTFINKGEIVKRLISRYHNPGLVADEGDRNAGRIEFALC

SGDDFTDEDMFRSLNGVSGSVLDADHVFTVTVGPSTKVTLARWHLLEPA

DVVDCVTLLSEQKGHLALERMGEVNLAALSSVEGHIPTA

The amino acid sequence of the *S. cerevisiae* Tps2 protein is shown below as SEQ ID NO: 3:

MTTTAQDNSPKKRQRIINCVTQLPYKIQLGESNDDWKISATTGNSALFS

SLEYLQFDSTEYEQHVVGWTGEITRTERNLFTREAKEKPQDLDDDPLYL

TKEQINGLTTTLQDHMKSDKEAKTDTTQTAPVTNNVHPVWLLRKNQSRW

RNYAEKVIWPTFHYILNPSNEGEQEKNWWYDYVKFNEAYAQKIGEVYRK

GDIIWIHDYYLLLLPQLLRMKFNDESIIIGYFHHAPWPSNEYFRCLPRR

KQILDLGVGANRICFQNESFSRHFVSSCKRLLDATAKKSKNSSNSDQYQ

VSVYGGDVLVDSLPIGVNTTQILKDAFTKDIDSKVLSIKQAYQNKKIII

GRDRLDSVRGVVQKLRAFETFLAMYPEWRDQVVLIQVSSPTANRNSPQT

IRLEQQVNELVNSINSEYGNLNFSPVQHYYMRIPKDVYLSLLRVADLCL

ITSVRDGMNTTALEYVTVKSHMSNFLCYGNPLILSEFSGSSNVLKDAIV

VNPWDSVAVAKSINMALKLDKEEKSNLESKLWKEVPTIQDWTNKFLSSL

KEQASSNDDMERKMTPALNRPVLLENYKQAKRRLFLFDYDGTLTPIVKD

PAAAIPSARLYTILQKLCADPHNQIWIISGRDQKFLNKWLGGKLPQLGL

SAEHGCFMKDVSCQDWVNLTEKVDMSWQVRVNEVMEEFTTRTPGSFIER

KKVALTWHYRRTVPELGEFHAKELKEKLLSFTDDFDLEVMDGKANIEVR

PRFVNKGEIVKRLVWHQHGKPQDMLKGISEKLPKDEMPDFVLCLGDDFT

DEDMFRQLNTIETCWKEKYPDQKNQWGNYGFYPVTVGSASKKTVAKAHL

TDPQQVLETLGLLVGDVSLFQSAGTVDLDSRGHVKNSESSLKSKLASKA

YVMKRSASYTGAKV

The amino acid sequence of the *A. flavus* Tps2 protein is shown below as SEQ ID NO:4:

MSSEQRTTPAKIPSDQPDPVLVGPGVKVLGEEAYTKASTATPIPGGEKK

QSFTTDAPSYFSKTPGEKMSSESSNATPTTPAQAAKDARSRIELLRRLS

LRETPKVLEADLRQQHPGLRLSGRIISAAFCIPYKVYYRRESSWELKPR

PGTSALFDSLAYLGSEETNVVSHTLVGWTGEVEPVPEDTVPLQQIPINT

SAKLPAATNGTAKPLNKAAAPVPVDANQRPPSHPLLDGFTVSQDDRSRL

DAQLSSGRYGKIAPVWLSAETEIPEDTIFLEDQGRWRRYAERELYPLLH

-continued

```
YKQHGPTDGRSERNWWADYVRMNRLFADRILKEYQEGDIVWIHDYHLFL
LPSMLRQRIPNIYIGFFLHAPFPSSEFMRCLAKRKEVLTGVLGANMIGF
QTFSYSRHFSSCCTRVLGFDSNSAGVDAYGAHVAVDVFPIGIDAKAIQN
IAFGASEIENAVTGIRKLYAGKKIIVGRDRLDSVRGVAQKLQSFEVFLE
RYPEWRDKVVLIQVTSPTSVEEEKEENKIASQISNLVSTINGRFGSLSF
SPVKYYPQYLSQHEYFALLRVADVGLITTVRDGMNTTSLEYIICQQQSH
GPLILSEFSGTAGTLSSAIHINPWDTAGVAGAINQALTMSPESKKASHQ
KLYKHVTTNTVSAWSTQYLSRLLTNLSSFDQSVATPALDRAKLLKQYRK
ARKRLFMFDYDGTLTPIVKDPQAAIPSDRVLRTIKTLAADSRNAVWIIS
GRDQAFLDEWMGHIPELGLSAEHGCFIRKPRSDDWENLAERSNMGWQKE
VMEIFQHYTERTQGSFIERKRVALTWHYRRADPEYGAFQARECRKHLEE
TVGKRWDVEVMAGKANLEVRPTFVNKGFIASRLVNEYGTGPGQAPEFIF
CSGDDFTDEDMFRALQKFDLPQDHVYSVTVGASSKQTSASWHLLEPADV
IETVTMLNSSSTQDY
```

The amino acid sequence of the *A. oryzae* Tps2 protein is shown below as SEQ ID NO:5:

```
MSSEQRTTPAKIPSDQPDPVLVGPGVKVLGEEAYTKASTATPIPGGEKK
QSFTTDAPSYFSKTPGEKMSSESSNATPTTPAQAAKDARSRIELLRRLS
LRETPKVLEADLRQQHPGLRLSGRIISAAFCIPYKVYYRRESSWELKPR
PGTSALFDSLAYLGSEETNWSHTLVGWTGEVEPVPEDTVPLQQIPINTS
AKLPAATNGTAKPLNKAAAPVPVDANQRPPSHPLLDGFTVSQDDRSRLD
AQLSSGRYGKIAPVWLSAETEIPEDTIFLEDQGRWRRYAERELYPLLHY
KQHGPTDGRSERNWWADYVRMNRLFADRILKEYQEGDIVWIHDYHLFLL
PSMLRQRIPNIYIGFFLHAPFPSSEFMRCLAKRKEVLTGVLGANMIGFQ
TFSYSRHFSSCCTRVLGFDSNSAGVDAYGAHVAVDVFPIGIDAKAIQNI
AFGASEIENAVTGIRKLYAGKKIIVGRDRLDSVRGVAQKLQSFEVFLER
YPEWRDKVVLIQVTSPTSVEEEKEENKIASQISNLVSTINGRFGSLSFS
PVKYYPQYLSQHEYFALLRVADVGLITTVRDGMNTTSLEYIICQQQSHG
PLILSEFSGTAGTLSSAIHINPWDTAGVAGAINQALTMSPESKKASHQK
LYKHVTTNTVSAWSTQYLSRLLTNLSSFDQSVATPALDRAKLLKQYRKA
RKRLFMFDYDGTLTPIVKDPQAAIPSDRVLRTIKTLAADSRNAVWIISG
RDQAFLDEWMGHIPELGLSAEHGCFIRKPRSDDWENLAERSNMGWQKEV
MEIFQHYTERTQGSFIERKRVALTWHYRRADPEYGAFQARECRKHLEET
VGKRWDVEVMAGKANLEVRPTFVNKGFIASRLVNEYGTGPGQAPEFIFC
SGDDFTDEDMFRALQKFDLPQDHVYSVTVGASSKQTSASWHLLEPADVI
ETVTMLNSSSTQDY
```

The amino acid sequence of the *A. clavatus* Tps2 protein is shown below as SEQ ID NO:6:

```
MSASQDSPSAKVLDGQPNPVIVGPGMKSLGEDAYTQAANVTPSLDTDKK
HPVDSDAPSYFANIPDTQPSADVNSPATPADAAKSAKSPIELLHRLSLN
RTPLVPDFDPREQYPGLNLTGRFISAAFCIPYKVVYRPGSDWELKPRPG
TSALFDSFAYLGSEETKWSHTLVGWTGEVEPIQETPASLQQIPVNAGAK
LPPALNGVAVPLSKAAAPVPVDSSQRPPSHPLLEGFTVPQEDRARLDGQ
LGSGRYGKIAPVWLSDESEEPEESSTIFLEDQGKWRRYAEKELYPLLHY
KQHGPTDGRSERKWWGDYVRMNRLFADRILEEYKEGDIVWIHDYHLFLL
PSLLRQRIPNIYIGFFLHAPFPSSEFMRCLAKRKEVLTGVLGSNMIGFQ
TFSYSRHFSSCCTRVLGFESNSAGVDAYGAHVAVDVFPIGIDVKAIQKA
AFGPANIENAVVALRNLYAGKKIIVGRDRLDSVRGVAQKLQAFEAFLER
YPEWRDKVVLIQVTSPTSVEEEKEDPENKIASQISNLVSTINGRFGSIS
FSPVKYYPQYLSQHEYFALLRVADVGLITTVRDGMNTTSLEYILCQQNT
HSPLILSEFSGTAGPLSSAIHINPWDTIGVAEAINEALTMSPEEKRLQH
VHLYKHVTTNTVLTWSNQFVTRLLTNLSSFDQSVATPALDRATVLKQYR
KARKRLFMFDYDGTLTPIVKDPQAAIPSDRVLRNIKTLAADPRNAVWII
SGRDQAFLDEWMGHIPELGLSAEHGCFIRKPRSDDWENLAESSDMGWQK
EVVEVFQHFTERTQGSFIERKRVALTWHYRRADPEYGAFQARECRKQLE
ETVAKRWDVEVMAGKANLEVRPTFVNKGFIASRLVDEYGTGPGQAPEFV
LCLGDDFTDEDMFRALKKANLPADHVYSVTVGASSKQTEASWHLLEPAD
VIGTISVLNNSSSAQEY
```

The amino acid sequence of the *T. stipitatus* Tps2 protein is shown below as SEQ ID NO:7:

```
MASEQGAPDKIPPNQPNPVIVGPGLSALGEEAYVDASTATPAVVPATTT
TANADGAADSYFSQVPGTATAIKDAYAKSPMSPADAASGVTSGPELLRR
LSLMGGAHLTPATPVTDPRADHPGLQLTGRIISASLCIPYKVAHQPGAD
WELSPRSGTSALFDSFAHLASDRSPWNHTLVGWTGEVEEIVSKRAPLQP
VSANGVPTAPLPVNKASAPVPVDLSQQVQSPVDGVLVSAADRERLERQL
KSSKYGRILPVWAIPESDEPQDDILLQDQSRWRRYAERELYPLLHYKQN
GPSDGRSERKWWTDYMRLNRLFADRIAGTYQAGDIVWIHDYHLFLLPNL
LRQRIPNIFIGFFLHSPFPSSEYMRCLAKRKEVLTGVLGANMIGFQTYS
YSRHFSSCCTRVLGFESNSAGVDAYGAHVAVDVFATGIDAQNVQRAAFG
SAETEQVVANIKKLYAGKKIIVGRDRLDSVRGVAQKLQAFEAFLEKYPH
WHDKVVLIQVTSPTSMEEQKEDPENKIGSQVSSLVSTINGRFGSLSFTP
VQYHPQYISPQEYFSLLRVADVGLITSVRDGMNTTSLEYVLCQQGNHGP
LILSEFSGTAAMLTSAIHINPWDTSGVAAAIDQALSMSEKEKVERHQVA
YRHVTSNTVSMWSQHYLNRLLTNLSSFDQSIATPALDRAQVLKQYRKAK
KRLFMFDYDGTLTPIVKDPQAAIPSDRVLRNIKSLAADPRNSVWIISGR
DQAFLDEWMGHIPELGLSAEHGCFIRKPRSDDWENLAAQSDMSWQKDVM
DIFQHYTERTQGSFIERKRVALTWHYRRADPEYGAFQAKECRKHLENTV
MKKYDVEVMAGKANLEVRPTFVNKGFIVTRLLNEYAKGEAPEFMFCSGD
DFTDEDMFRALRHSNLPQEHIFSVTVGASSKQTLASWHLLEPADVIATI
GMLNGTSMGAEYS
```

In some embodiments of the present compositions and methods, the amino acid sequence of the Tps2 protein that is altered in production levels has a specified degree of overall amino acid sequence identity to the amino acid sequence of SEQ ID NOs: 1, 2, 3, 4, 5, 6, or 7, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NOs: 1, 2, 3, 4, 5, 6, or 7. The nucleotide sequences encoding each amino acid sequence can be identified from a BLAST search for each corresponding protein as is know to one skilled in the art.

In some embodiments of the present compositions and methods, the tps2 gene that is disrupted encodes a Tps2 protein that has a specified degree of overall amino acid sequence identity to the amino acid sequence of SEQ ID NOs: 1, 2, 3, 4, 5, 6, or 7, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NOs: 1, 2, 3, 4, 5, 6, or 7.

The amino acid sequence information provided herein readily allows the skilled person to identify a Tps2 protein, and the nucleic acid sequence encoding a Tps2 protein, in any filamentous fungi, and to make appropriate disruptions in the tps2 gene to affect the production of the Tps2 protein. The polynucleotide sequences encoding SEQ ID NOs: 1, 2, 3, 4, 5, 6, or 7 can be found in the GenBank or JGI databases, as are known to one of skill in the art.

In another aspect, a method for altering the morphology of filamentous fungus cells is provided. The variant filamentous fungus cells exhibit altered growth morphology on solid medium and produce cell broth having different viscosities when grown in submerged culture compared to parental cell growth and cell broth viscosities.

In some cases, the method comprises disrupting the tps2 gene in a parental strain using suitable genetic methods, wherein during aerobic fermentation the disrupted tps2 variant strain produces during aerobic fermentation in submerged culture a cell broth that requires reduced agitation to maintain a preselected dissolved oxygen content, or maintains an increased dissolved oxygen content at a preselected amount of agitation, compared to the cells of the parental strain. Such methods can be used to disrupt the tps2 gene in any manner described above and elsewhere as are known to one of skill in the art. Preferably, disruption of the tps2 gene is performed by genetic manipulation using sequence-specific molecular biology techniques, as opposed to chemical mutagenesis, which is generally not targeted to specific nucleic acid sequences. However, chemical mutagenesis can be used to achieve satisfactory results.

In some embodiments, the parental strain into which the reduced viscosity phenotype is introduced creating a reduced viscosity strain already comprises a gene of interest intended to be expressed at high levels. In this manner, the present methods obviate the need to introduce a gene of interest into a pre-existing reduced viscosity strain for production. Thus, the present methods can be used to produce a reduced viscosity variant strain of filamentous fungus cells from a parental strain already comprising a gene of interest.

VI. Utility

The use of reduced viscosity strains of filamentous fungi is known to improve the distribution of oxygen and nutrients in a submerged culture, reduce the amount of energy required to agitate a submerged culture, and increase the cell mass present in the culture, leading to increased protein production. Moreover, the present variant strains of filamentous fungus offer significant advantages over previously-described reduced viscosity strains.

First, the present variant strains can have a fully defined genome, making them well-suited for subsequent genetic manipulation, complementation, mating, and the like Second, the present strains are still capable of high levels of protein production, for example, by the manipulation(s) that resulted in the attendant viscosity alteration. Third, reduced viscosity strains can be produced from essentially any parental strain, including parental strains that already produce a protein intended for high level expression (i.e., a protein of interest), already encoding a selectable marker, or already including other features that are desirable in a production host. Thus, the present strain and methods eliminate the need to transfer a gene encoding a protein of interest into a preexisting reduced viscosity production strain.

The present strains and methods find use in the production of commercially important protein in submerged cultures of filamentous fungi. Commercially important proteins include, for example, cellulases, xylanases, pectinases, lyases, proteases, kinases, amylases, pullulanases, lipases, esterases, perhydrolases, transferases, laccases, catalases, oxidases, reductases, chlorophyllases, hydrophobin, chymosin, carbonic anhydrase, hymidylate synthase, dihydrofolate reductase, tyrosine kinases, multi-drug resistance proteins (e.g., ABC P-gp proteins), CAD (carbamyl-P synthase, aspartate transcarbamylase, dihydroorotase), topoisomerases, ribonucleotide reductase, and antibodies and other enzymes and non-enzyme proteins capable of being expressed in filamentous fungi. Such proteins can be suitable for industrial, pharmaceutical, animal health and food and beverage use.

The following numbered paragraphs further describe various aspects and embodiments of the present compositions and methods. The subject matter of each of the numbered paragraphs can be used alone or in combination with the subject matter of any other numbered paragraph, as indicated.

1. In one aspect, a variant strain of filamentous fungus derived from a parental strain is provided, the variant strain comprising a genetic alteration that causes cells of the variant strain to produce an altered amount of functional Tps2 protein compared to cells of the parental strain, wherein the cells of the variant strain produce during aerobic fermentation in submerged culture a cell broth that (i) requires an altered amount of agitation to maintain a preselected dissolved oxygen content compared to the cells of the parental strain, and/or (ii) maintains an altered dissolved oxygen content at a preselected amount of agitation, compared to the cells of the parental strain.

2. In some embodiments of the variant strain of paragraph 1, the altered amount of functional Tps2 protein is a reduced amount, and the variant strain produces during aerobic fermentation in submerged culture a cell broth that (i) requires reduced agitation to maintain a preselected dissolved oxygen content compared to the cells of the parental strain, and/or (ii) maintains an increased dissolved oxygen content at a preselected amount of agitation, compared to the cells of the parental strain.

3. In some embodiments of the variant strain of paragraphs 1 or 2, the genetic alteration comprises a disruption of the tps2 gene present in the parental strain.

4. In some embodiments of the variant strain of paragraph 3, disruption of the tps2 gene is the result of deletion of all or part of the tps2 gene.

5. In some embodiments of the variant strain of paragraph 3, disruption of the tps2 gene is the result of deletion of a portion of genomic DNA comprising the tps2 gene.

6. In some embodiments of the variant strain of paragraph 3, disruption of the tps2 gene is the result of mutagenesis of the tps2 gene.

7. In some embodiments of the variant strain of any of paragraphs 3-6, disruption of the tps2 gene is performed using site-specific recombination.

8. In some embodiments of the variant strain of any of paragraphs 3-7, disruption of the tps2 gene is performed in combination with introducing a selectable marker at the genetic locus of the tps2 gene.

9. In some embodiments of the variant strain of any of paragraphs 1-8, the variant strain does not produce functional Tps2 protein.

10. In some embodiments of the variant strain of any of paragraphs 1-8, the variant strain does not produce Tps2 protein.

11. In some embodiments of the variant strain of any of paragraphs 1-10, the variant strain further comprises a gene encoding a protein of interest.

12. In some embodiments of the variant strain of any of paragraphs 1-11, further comprising a disruption of the sfb3 gene.

13. In some embodiments of the variant strain of any of paragraphs 1-12, further comprising a disruption of at least one gene selected from the group consisting of the sfb3 gene, the seb1 gene, the mpg1 gene, the gas1 gene, and the crz1 gene.

14. In some embodiments of the variant strain of any of paragraphs 1-13, the variant strain produces substantially the same amount of, or more, protein per unit amount of biomass as the parental strain.

15. In some embodiments of the variant strain of any of paragraphs 1-14, the filamentous fungus is a Pezizomycotina species.

16. In some embodiments of the variant strain of any of paragraphs 1-15, the filamentous fungus is a *Trichoderma* spp.

17. In some embodiments of the variant strain of any of paragraphs 1-16, the filamentous fungus is *Trichoderma reesei*.

18. In another aspect, a method for producing a variant strain of filamentous fungus cells is provided, comprising: introducing a genetic alteration into a parental strain of filamentous fungal cell, which genetic alteration alters the production of functional Tps2 protein compared to the cells of the parental strain, thereby producing a variant filamentous fungal cell that produces during aerobic fermentation in submerged culture a cell broth that (i) requires an altered amount of agitation to maintain a preselected dissolved oxygen content, compared to the cells of the parental strain, and/or (ii) maintains an altered dissolved oxygen content at a preselected amount of agitation, compared to the cells of the parental strain.

19. In some embodiments of the method of paragraph 18, the genetic alteration reduces or prevents the production of functional Tps2 protein, thereby producing a variant filamentous fungal cell that produces during aerobic fermentation in submerged culture a cell broth that (i) requires reduced agitation to maintain a preselected dissolved oxygen content, compared to the cells of the parental strain, and/or (ii) maintains an increased dissolved oxygen content at a preselected amount of agitation, compared to the cells of the parental strain.

20. In some embodiments of the method of paragraph 18 or 19, the genetic alteration comprises disrupting the tps2 gene in a parental filamentous fungal cell using genetic manipulation.

21. In some embodiments of the method of any of paragraphs 18-20, the genetic alteration comprises deleting the tps2 gene in a parental filamentous fungal cell using genetic manipulation.

22. In some embodiments of the method of any of paragraphs 18-21, the genetic alteration is performed using site-specific genetic recombination.

23. In some embodiments of the method of any of paragraphs 18-22, disruption of the tps2 gene is performed in combination with introducing a selectable marker at the genetic locus of the tps2 gene.

24. In some embodiments of the method of any of paragraphs 18-23, disruption of the tps2 gene is performed in combination with disrupting the sfb3 gene.

25. In some embodiments of the method of any of paragraphs 18-24, disruption of the tps2 gene is performed in combination with disruption of at least one gene selected from the group consisting of the sfb1 gene, the seb1 gene, the mpg1 gene, the gas1 gene, and the crz1 gene.

26. In some embodiments of the method of any of paragraphs 18-25, the variant strain produces substantially the same amount of, or more, protein per unit amount of biomass as the parental strain.

27. In some embodiments of the method of any of paragraphs 18-26, the filamentous fungus is a Pezizomycotina species.

28. In some embodiments of the method of any of paragraphs 18-27, the filamentous fungus is a *Trichoderma* spp.

29. In some embodiments of the method of any of paragraphs 18-28, the filamentous fungus is *Trichoderma reesei*.

30. In some embodiments of the method of any of paragraphs 18-29, the parental strain further comprises a gene encoding a protein of interest.

31. In some embodiments of the method of paragraph 30, the gene encoding the protein of interest is present in the parental strain prior to introducing the genetic alteration that reduces or prevents the production of functional Tps2 protein.

32. In another aspect, a protein of interest produced by the variant strain of paragraph 11 is provided.

33. In another aspect, a variant strain of filamentous fungus produced by the method of any of paragraphs 18-31 is provided.

34. In another aspect, a variant strain of filamentous fungus derived from a parental strain is provided, the variant strain comprising:
(a) a genetic alteration that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, and
(b) a gene encoding a protein of interest, wherein the gene encoding the protein of interest is present in the variant strain prior to the genetic alteration in (a).

35. In some embodiments of the variant strain of paragraph 34, the genetic alteration comprises a disruption of the tps2 gene present in the parental strain.

36. In some embodiments of the variant strain of paragraph 35, disruption of the tps2 gene is performed in combination with introducing a selectable marker at the genetic locus of the tps2 gene.

37. In some embodiments of the variant strain of paragraph 35 or 36, disruption of the tps2 gene is performed in combination with disrupting at least one gene selected from the group consisting of the sfb3 gene, the seb1 gene, the mpg1 gene, the gas1 gene, and the crz1 gene.

38. In some embodiments of the variant strain of any of paragraphs 35-37, disruption of the tps2 gene is performed in combination with disrupting the seb1 gene.

These and other aspects and embodiments of the present strains and methods will be apparent to the skilled person in view of the present description. The following examples are intended to further illustrate, but not limit, the strains and methods.

EXAMPLES

Example 1

Deletion of the Tps2 Gene from *T. reesei* Mutant Morph 77B7

A *Trichoderma reesei* Morph strain was deleted for four major cellulase genes, including cbhI, cbhII, egII and egIV, which makes it particular suitable for expressing other proteins in the absence of or in reduced cellulase background. See, WO 05/001036.

A. TrGA Producing Strain Morph 77B7

The Morph strain, described above, was previously transformed with a native *Trichoderma* glucoamylase gene (TrGA) under control of the CBH1 promoter, using amdS as a marker. A transformant containing two tandem copies of glucoamylase (TrGA 29-9) was subsequently isolated, and random chemical mutagenesis was used to produce a mutant (77B7). A spontaneous pyr2 mutant derivative was subsequently isolated by 5-fluoro-orotic acid (FOA) selection.

B. Generation of a Tps2 Disruption Cassette

The *Trichoderma reesei* tps2 (PID 48707) was deleted from mutant Morph 77B7.

The tps2 disruption cassette plasmid pRATT251 (FIG. 1) was prepared using standard molecular biology procedures. This plasmid included a DNA sequence having a 2.8 Kb region homologous to the DNA sequence spanning part of the 5' untranslated region and contiguous upstream sequences (Left Flank). Also included within the plasmid was a DNA sequence having a 2.5 Kb region homologous to the DNA sequence spanning part of the second exon of the tps2 gene and contiguous downstream sequences (Right Flank). These sequences were designed to target the tps2 gene and replace the regions of the genome between the Left and Right Flanks, region 1135546 to 1136670 on Scaffold 10 (JGI *T. reesei* genomic database v2), with the intervening cassette sequences. These intervening sequences included a pyr2 selection marker from *Trichoderma atroviride* intended to minimize homology to the endogenous *T. reesei* pyr2 in the genome of the strain to be transformed Immediately upstream of the pyr2 selection marker was a directly repeated duplication of the 3'end of the marker, which facilitated the subsequent loss of the marker and isolation of useful pyr2 mutant derivatives of the transformants/disruptants. This full tps2 disruption cassette was amplified by PCR using primers RPG398 and RPG401. Multiple PCR reactions were pooled and cleaned using standard molecular biology procedures for use in the subsequent steps.

The nucleic acid sequence of the tps2 gene was obtained from the JGI data base: Protein ID: 48707, Name: estExt_Genewise1.C_100658, available at http://genome.jgi-psf.org/cgi-bin/dispGeneModel?db=Trire2&id=48707, (The Genome Portal of the Department of Energy Joint Genome Institute I. V. Grigoriev, H. Nordberg, I. Shabalov, A. Aerts, M. Cantor, D. Goodstein, A. Kuo, S. Minovitsky, R. Nikitin, R. A. Ohm, R. Otillar, A. Poliakov, I. Ratnere, R. Riley, T. Smirnova, D. Rokhsar, and I. Dubchak. Nucleic Acids Res 2011 0: gkr947v1-gkr947) as disclosed below. The untranslated region is italicized and flanked 5' and 3' by upstream or downstream sequence, coding regions are in bold and introns are in lower case (SEQ ID NO: 14):

AGCTCCCGATAGGGCGGCGGCCAAGTCACAGGCCATCTCAGCAAAGACG

AGGCCGAGAACATCAATCGACGGAAAGGAGATAAACGTTGCGCCCCCCC

AGAATACTAGCCGTCGTCTTAAGCCACACTCCTTCTCACCCTTCCCTCC

TCCTGCCCATTCTCTCCCTGAACCCGCACAACTCCAGGAGCAGCTGTGA

CTCCTCCTGCCTCTCCTCTTCTCCTCGTCGTCCACACGTAGCAGGTGCT

CGCTGTCGGTCAACAGTTTGAGCCTTCCCTCAGCAGCCGGCACCAAGCC

TCCGAAGCGCTTGGCACCACAGTACGAGGCCAAGCACCGCCTAACGCCC

TTCTGCCAGCCGCTGACCTTGTACCCCTCCCCCTCCTCCAGCACAGGTT

CCTCGAGACTTTGCAAGCACCGACCGACGTCGACAAGACACAAACACAA

AACCATCCGGGAACCTCGCGCGCAACCGGCACAATGGCGCGCCGTGAGT

CTCTGTCTGAGATTCGCGCCGCCAACCCCGAGCTCTTCCTGACGGGCAA

CATCATCTCGGCGACCTTCAACATCCCCCATGCTGTGACATACCACAAG

GGCGGTGCTTGGgtgagtgcattttcctggctgggcatcgctttgagga cgtcctaagcttgtctgtgcttgaagcacttggcactggtcgaggcgag atcaaggcagacgagctttgtttgattttctgagacatctccctcctcc ctctgcgttgattgcctcattctgctgctctcctccgtcgccccgccc gtgggaagccatcattctgactgactaggctgcgcagGATCTGAAGCCC

CGCCGTGGCCAGTCGGCCCTCATCGACTCCTTCGCCTATCTCTCGTCCG

ACGCGACGCCCTGGAATCACACAGTCGTGGCCTGGACAGGCGAAATTGC

CAACCCCGACAACGACCCGCTGTCTCCTCCAGATACCCCCTCAGCCGCG

GCCACCACCATCGGTGCTGCCAACTCGCTGTCGGCTCCCGTCCCGATCG

ATGCCACCACTCGGCTGCCCACGCCTCCCCCAGTCGACGGGCTCTGGAT

CCCCAAGGCAGACCAGACGCGGCTGGAGCACCAGCTGTCCCACAGCACA

ACCATTCGCACCGTGCCTGTCTGGCTGGCTGACCAGAGCGAGGCCACCG

ATGATGGCATCATGCTCAAGGACCAGGCTCGCTGGAGGCGCTATGCTGA

GCACGATCTCTACACACTCTTCCACTACAAGCAGCACGAGCCCACGGAT

GGCCGCAAGGAGCGGGCGCAGTGGGCCGACTACTACCGCATGAACCAGA

AGTTCGCCAACAAGATCATTGAGATCTACAAGCCTGGTGACGTTGTCAT

CGTTCATGATTACTATCTGATGCTGCTGCCCAGCATGCTCCGCCAGCGG

GCTCCCAAGATGTACATCTCCTTCTTCCTCCACTCGCCCTTCCCCAGCA

GCGAGTTCCTCCGTTGCCTGCCCCGCCGCAAGGAGGTGCTTGAGGGTGT

CCTGGGCGCCAATCTCGTGGGCTTCCAGTCTTACAGCTACTCGCGCCAC

-continued

```
TTCCTCAGCTGCTGCACCCGCATCCTCGGTTTCCCCTCTGACACTCTTG

GCATCGACGCCTATGGCTCCAGGGTGCAGGTCGGAGTGTTTCCCATTGG

CATCGACGCCGCCAAGGTGGAGACCGCCGCCTGGGCGGACACCGTCAAC

GAGAAGCACGCTGCCGTCCTGAAGATGTACGAAGGCAAGAAGATCATCG

TCGGCCGAGATCGTTTGGACAGCGTGAGGGGCGTTGCTCAAAAGCTGCA

GGCGTTTGAGCGCTTCCTGGAGCTGTACCCTCACTGGCGCGAGAAGGTG

GTCCTGATCCAGGTCACGTCGCCCACCAGCATCGAGGCTGAGAAGGGTG

ACCCGGAGAACAAGAACGCCAGTCGAGTCAACGAGCTCATCACCAAGAT

CAATGGCGAATACGGCAGTCTCGGCTTTTCGCCTGTGCAGCACTACCCC

CAGTACCTCAGCCAGGCCGAGTACTTTGCCTTGCTCCGGGCCGCAGACA

TTGGCCTCATCACCTCGGTGCGAGATGGAATGAACACGACAAGTCTCGA

GTACGTTGTCTGCCAGAAGGATAGCAACGGCCCACTCATTCTCTCCGAG

TTCAGCGGCACCGCGGGTAGTCTCCGCGACGCCATCCACATCAACCCCT

GGGATCTGACGGGCGTGGCGGAAAAGATCAACGCGGCTCTGGAGATGTC

TGAGGAGGAGCGCGTCAAGATGCAGACAAGCCTCTACACCCACGTCACG

ACGCAGAATGTCCAGTCGTGGATCACCAAGTTCATCCGCAAGTTCCACG

CGGCGCTGAGCGAGACCAACTCAGTCACATCGACACCCCTTCTCGACCG

CGCGCTCTTGCTGTCCCGTTACCGCGCCGCCAAGAAGCGCCTGTTCATG

TTTGACTACGACGGCACCCTCACGCCCATTGTGCGCGAACCGAGCGCCG

CTGTTCCTTCGGAGCGCATCATCCGCTACCTGCAGTCGCTTGCATCGGA

CCCCAGGAACGCGGTCTGGATCATCTCTGGCCGAGACCAAGAGTTCCTT

CAGCAACATCTCGGCCACATCCCCCGGATCGGATTCTCTGCCGAGCATG

GTAGTTTCATGCGAGACCCCGGCAGCGACGAGTGGGTTAACCTGGCAGA

GAAGTTTGACATGGGCTGGCAGGCAGAGGTCATGGAGGTGTTCCAGCGT

TACACGGACAAGGTTCCAGgtgagttgctgtctatcccgagtttgagtt gcctcaaagaacaatcctatcacgggttaaggcaagacaagacagaaag cagaagctaacacactatccttagGTTCCTTCATCGAGCGAAAACGCTG

CGCCCTGACCTGGCATTATCGACTGGCCGAGCCGGAGCAAGGCCTCCAC

ATGTCACGCGAGTGTCACCGAGAGCTCGAGACCGGCATTGCCCAGCGAT

GGGAGGTCGAGGTGATGCCTGGCAAGGCCAACATCGAGGTGCGCCCTAC

GTTCATCAACAAGGGTGAGATCGCCAAGCGACTGGTGGCCACTTATCAC

AACCCGGGAGCCGCCCCGACCGACAAGGACCCTTACCCCGGAAAGATTG

AGTTTGCTCTCTGCTCTGGAGACGACTTTACCGACGAGGACATGTTCCG

CAGCCTCAACGGAGCATGTGGCACGATCCTGGAAGACCAGCACGTCTTC

ACCGTCACTGTGGGAGCCAGCACCAAGGTGACGCTGGCCAAATGGCATC

TCCTGGAGCCCGAGGACGTGATTGAGTGCGTGGGTCTGCTGGCTGGTGC

TGGCGACCCGGCCAGCCTCGAGCGTGTTGGAGAGGTGAACCTGGCCGCT

TTGAGCCAGGTGGAGGGTCACATTCCCGCCGAGGAGCTGTAAAGGACAT

TCGTTTGTCCCAGTGCTTTCAGGCGTGGAATGGCCTCTTGATGGGAAAC

CACGAGGCTTTCTCCAGATGCTGAACTTGAGTGTTTGGCAAAGTCTGGG

GGTGATTCTTTTCCTTTTGACGACTTGCACATTTGAGATGAAGAGAGCG

AAAACGGACGCATAGAACGGTAATAGAAACGAAGGATGGCGCGTGGCGT

ACGGGCTAGTAATGACCTTGTGGCACAGAATCTGTGATAAAGAGTAAAA

AAAAAGGAAACAAAGGCCCCCCCGAGAGACAGAAAAATATCAAAAGAAG

AAGAAAAAAAAAAAAAAATCACGGCAGCAAATACGGGACAAAAAGGGG

ATTGCGGACGCTCTGGTAATCTGACATGGAAAGTTCCGCGATGAACTGG

CAAAGTATACAGAGTAGCATCAGTCGCGATTCATTTAGCGTGGAGAATA

AGACAAAGTTTAACCTCGACTTGTGTTGCACTGCAGCTGAGTTTCAATC

TTGAATC
```

C. Generation of Strain Morph 77B7 Δtps2

Strain Morph TrGA 77B7 Δpyr2 was transformed with the tps2 disruption cassette using PEG-mediated transformation, and plated on Vogel's minimal medium containing sorbitol to select for candidates based on uridine prototrophy acquired by the pyr2 marker. Individual transformants were isolated and propagated by transfer to Vogel's minimal medium. PCR analysis was used to identify transformants in which the tps2 disruption cassette integrated at the tps2 locus by homologous recombination. Homologous integration of the Δtps2 disruption cassette at the tps2 locus was verified by amplifying DNA fragments of the expected sizes using two primer pairs. Primer pair RPG408 and RPG253 amplified a DNA fragment starting outside the 5' end of the disruption cassette region and ending within 3' region. Primer pair RPG409 and RPG273 amplified a DNA fragment starting within the 5' region of the disruption cassette and ending outside the 3' end of the disruption cassette region. The generated strain with confirmed homologous integration of the tps2 disruption cassette was named Morph 77B7 Δtps2.

TABLE 1

Primers used in example 1

| Primer | Sequence | SEQ ID NO: |
|---|---|---|
| RPG398 | 5'-CCCCTCCGGAGCGTGGGTGGTCACGTGATACTG-3' | 8 |
| RPG401 | 5'-GGCCTCTAGACCGGAGACGCACGATTCAAGATT-3' | 9 |
| RPG408 | 5'-GTCGCGATCGATGGCTGATTGTC-3' | 10 |
| RPG253 | 5'-TTCCTGACAACGAGGACATCTCAAGCTGT-3' | 11 |
| RPG409 | 5'-TCACCGGTCGGATTCGCCTAGTT-3' | 12 |
| RPG273 | 5'-GGTCAGTAACATAGCAGGACTATAGTAGTGGCTCAC-3' | 13 |

Morph 77B7 Δtps2 obtained from the above procedure was observed to have altered morphology in liquid culture having shorter filaments than the Morph 77B7 parent. In liquid medium, cultures containing the Morph 77B7 Δtps2 mutant also showed a higher level of dissolved oxygen during growth compared to cultures containing the Morph 77B7 parent (Table 2).

Strains Morph 77B7 and Morph 77B7 Δtps2 were grown under similar conditions in submerged (liquid) culture, and their growth phenotypes were compared. Briefly, spores of each strain were added separately to 500-mL of minimal medium in a 3-L flask with both side and bottom baffles.

After autoclaving for 30 minutes, sterile 60% glucose was added to a final concentration of 27.5 g/L. The cultures were grown for 48 hrs at 34° C. in a shaking incubator.

After 48 hrs, the contents of each flask were added separately to 14-L fermentors containing 9.5 L of medium containing 4.7 g/L KH$_2$PO$_4$, 1.0 g/L MgSO$_4$.7.H$_2$O, 4.3 g/L (NH$_4$)$_2$SO$_4$ and 2.5 mL/L of the same trace element solution. These components were heat sterilized together at 121° C. for 30 minutes. A solution of 60% glucose and 0.48% CaCl$_2$.2.H$_2$O was separately autoclaved, cooled, and added to the fermentor to a final concentration of 75 g/L glucose and 0.6 g/L CaCl$_2$.2.H$_2$O. The medium was adjusted to pH 3.5 with 28% NH$_3$ and the temperature was maintained at 34° C. for the entire growth period.

A dissolved oxygen (DO) probe was calibrated to 100% when there was no added pressure in the headspace (i.e., 0 bar gauge, 1 bar absolute). The pressure in the headspace was then set to 0.7 bar (gauge), after which the oxygen probe read 170% before the seed culture was added. The fermentor contained two, four-blade turbines that provided mixing via a variable speed motor that was initially set at 500 rpm.

As the cultures grew, DO content levels dropped, at least partly as a consequence of the increased viscosity of the broth due to the proliferation of filamentous fungus hyphae. When DO content level fell below 40%, the agitation rate was increased to maintain the DO content level at 40%. Upon reaching 750 rpm agitation, DO content level would be allowed to drop below 40%. If the DO content level did not fall below 40%, then it was unnecessary to increase the agitation rate during the fermentation run, and the initial agitation rate was higher than necessary. When the glucose was completely consumed, the amount of biomass produced in each fermentor was measured, and found to be substantially the same for both strains.

The DO content level in each fermentor at a given level of agitation, and the amount of agitation required to maintain a given DO content level are indirect measures of the viscosity of the different broths, due to the different strain growth phenotypes. Although it would be ideal to vary only one variable (e.g., DO content or agitation) and measure the other, it is desirable to prevent the DO content level from falling below 40% to ensure the production of sufficient biomass in each fermentor, thereby permitting a more meaningful comparison among the growth characteristics of the different strains.

Generally, where it is necessary to increase the agitation rate to maintain a target DO content level, the amount of agitation can be estimated by the amount of power supplied to the motor driving the fermentor turbine, which provides a metric that correlates with the viscosity of the broth. In particular, the extra power required to agitate the suspended culture is proportional to the agitation rate raised to the 3rd power.

As shown in Table 2, Morph 77B7 Δtps2 has a reduction in broth viscosity compared to the parent Morph 77B7. At the end of the batch growth phase, when all the glucose has been consumed, both strains had achieved a similar biomass concentration. To arrive at the end of the batch growth phase, the Morph 77B7 control strain saw agitation increased to 616 rpm and then saw DO content level drop down to as low as 40%. The strain Morph 77B7 Δtps2 did not require as much energy to achieve the same biomass concentration. Agitation rate never increased above 500 rpm and the % DO never dropped below 110.

TABLE 2

Broth viscosity of Morph 77B7 compared to Morph 77b7 Δtps2

| Strain | Deletion | DO (%) | Agitation (rpm) | Biomass (g/kg) | CER (mmol/L/hr) |
|---|---|---|---|---|---|
| Morph 77b7 | none | 40 | 616 | 38 | 141 |
| Morph 77b7Δtps2 | tps2 | 110 | 500 | 41 | 94 |

Example 2

Additive Effect Produced by Altering at Least One of Sfb3, Seb1, Mpg1, Gas1, and Crz1 Production a. Viscosity Reduction in Disrupted Sbf3

The Sfb3 gene (also known as Lst1) has previously only been characterized in budding yeast (i.e., *Saccharomyces cerevisiae*), where it encodes a protein associated with the COPII protein coat surrounding transport vesicles that carry proteins from the endoplasmic reticulum to the Golgi apparatus. Sfb3, as well as Sfb2, are homologs of Sec24, all of which genes are involved with packaging specific cargo proteins into the vesicles.

As shown in Table 3, disrupting the sfb3 gene from strain 29-9 Δsfb3 resulted in a strain having a reduction in the highest agitation rate required to maintain the dissolved oxygen at 40% at the end of the growth phase. Under these growth conditions, the original strain, 29-9, required 2.6 times more power than either the 70H2 (chemically mutagenized 29-9) or 29-9 Δsfb3 strains in order to maintain a DO of 40% and produce the amount of biomass. Strains 70H2 and 29-9 Δsfb3 had similar viscosity properties, and produced similar levels of a protein of interest (TrGA) in suspended culture, demonstrating that a reduced viscosity growth phenotype can be imparted to a filamentous fungus by disrupting the sfb3 gene. Alterations in the Sfb3 protein resulting in alterations in viscosity are further described in PCT Publication No. WO 2012/027580 A1, published 1, Mar. 2012, filed as International Application No. PCT/US2011/049164, filed 25, Aug. 2011, incorporated herein by reference.

TABLE 3

Agitation rate required to maintain a DO of 40% at the end of the growth phase

| Strain | Agitation rate | Relative power increase from baseline at 500 rpm |
|---|---|---|
| 29-9 | 750 | $(750/500)^3 = 3.4$ |
| 70H2 | 539 | $(539/500)^3 = 1.3$ |
| 29-9 Δsfb3 | 540 | $(540/500)^3 = 1.3$ |

B. Viscosity Reduction in Disrupted Seb1

Seb1 from *Trichoderma atroviride* is a STRE-element-binding protein, and the seb1 gene is believed to be an orthologue of the yeast msn2/4 gene and the *Aspergillus nidulans* msnA gene. Notably, the seb1 gene cannot complement the msn2/4 gene in yeast, so is probably not a functional homologue (Peterbauer, C. et al. ((2002) Molecular Genetics and Genomics 268:223-31). Seb1 is involved with but not essential in the osmotic stress response but has been found to be associated with altered morphology, particularly those giving rise to a low viscosity phenotype when seb1 is disrupted. Details of the seb1 disruption can be found in U.S.

Provisional Application No. 61/478,160, filed Apr. 22, 2011, incorporated by reference herein in its entirety.

As shown in Table 4, deletion of the seb1 gene from strain Morph1/1 Δku80 resulted in a strain having a reduction in broth viscosity. At the end of the batch growth phase, when all the glucose has been consumed, both strains had achieved a similar biomass concentration. To get there, the control strain saw agitation increased to the maximum of 750 rpm and then saw DO drop down to as low as 29%. The seb1 deleted strain did not require as much energy to achieve the same biomass concentration. Agitation rate was never increased above 500 rpm and DO dropped only as low as 55%.

TABLE 4

Broth viscosity in Morph1/1 Δku80 with and without the seb1 gene

| Strain | Deletion | DO (%) | Agitation (rpm) | Biomass (g/kg) | CER (mmol/L/hr) |
|---|---|---|---|---|---|
| Morph1.1Δku80 | none | 29 | 750 | 38 | 157 |
| Morph1.1Δku80, Δpyr4, Δseb1 | seb1 | 55 | 500 | 37 | 138 |

C. Viscosity Reduction in Disrupted Mpg1

The mpg1 gene encodes a GTP:alpha-D-mannose-1-phoshate guanyltransferase. Over-expression of the mpg1 gene increases GDP-mannose levels, which can play a major regulatory role in early stages of protein glycosylation.

As shown in Table 5, MAGI 10-8 g, the mpg1 deletion variant strain, has a reduction in broth viscosity compared to the parent MAGI. At the end of the batch growth phase, when all the glucose has been consumed, both strains had achieved a similar biomass concentration. To get there, the MAGI control strain saw agitation increased to the maximum of 750 rpm and then saw DO drop down to as low as 35%. The strain MAGI 10-8 g did not require as much energy to achieve the same biomass concentration. Agitation rate was increased slightly to 513 rpm when the % DO dropped to 40%. Protein production was not adversely affected in MAGI 10-8 g compared to MAGI (not shown). Details of the mpg1 disruption can be found in U.S. Provisional Application No. 61/478,162, filed Apr. 22, 2011, incorporated by reference herein in its entirety.

TABLE 5

Broth viscosity of MAGI compared to MAGI 10-8 g

| Strain | Deletion | DO (%) | Agitation (rpm) | Biomass (g/kg) | CER (mmol/L/hr) |
|---|---|---|---|---|---|
| MAGI | none | 35 | 750 | 39 | 125 |
| MAGI 10-8 g | mpg1 | 40 | 513 | 40 | 128 |

D. Viscosity Reduction in Disrupted Gas1

The Gel/Gas/Phr family of fungal β(1,3)-glucanosyltransferases plays an important role in cell wall biogenesis by processing the main component β(1,3)-glucan (Popolo et al., 2008). gas1 (PID 22914) encodes a beta-1,3-glucanosyltransferase that is a GPI (and/or glucan)-anchored protein capable of breaking and joining beta-1,3-glucans. There are multiple paralogs in many fungal genomes including *T. reesei*, which has five. Separate studies have shown that mutation of the gas1 gene (or the gel1 gene as it is known in *Aspergillus fumigatus*) affects fungal cell wall structure, and can lead to morphological changes as well as hypersensitivity to Calcofluor White, Congo Red and sodium dodecyl sulfate (Schirawski, J. et al. 2005, Mouyna, I. et al. 2005).

A *Trichoderma reesei* Morph strain was deleted for four major cellulase genes, including cbhI, cbhII, egII and egIV, which makes it particular suitable for expressing other proteins in the absence of or in reduced cellulase background. See, WO 05/001036. The Morph strain had been previously transformed with a native *Trichoderma* glucoamylase gene (TrGA) under control of the CBH1 promoter, using amdS as a marker. A transformant containing two tandem copies of glucoamylase (TrGA 29-9) was subsequently isolated, and random chemical mutagenesis was used to produce a mutant (77B7). A spontaneous pyr2 mutant derivative was subsequently isolated by 5-fluoroorotic acid (FOA) selection. The *Trichoderma reesei* gas1 (PID 22914) was deleted from mutant Morph 77B7.

Strain Morph TrGA 77B7 Δpyr2 was transformed with a gas1 disruption cassette using PEG-mediated transformation, and plated on Vogel's minimal medium containing sorbitol to select for candidates based on uridine prototrophy acquired by the pyr2 marker. As shown in Table 6, Morph 77B7 Δgas1 has a reduction in broth viscosity compared to the parent Morph 77B7. At the end of the batch growth phase, when all the glucose has been consumed, both strains had achieved a similar biomass concentration. To arrive at the end of the batch growth phase, the Morph 77B7 control strain saw agitation increased to 616 rpm and then saw DO content level drop down to as low as 40%. The strain Morph 77B7 Δgas1 did not require as much energy (i.e., rpm increase in agitation) to achieve the same biomass concentration. Agitation rate never increased above 500 rpm and the % DO never dropped below 115. Protein production was not adversely affected in Morph 77B7 Δgas1 compared to Morph 77B7 (data not shown). Details of the gas1 disruption can be found in U.S. Provisional Application No. 61,480, 602, filed Apr. 29, 2011, incorporated by reference herein in its entirety.

TABLE 6

Broth viscosity of Morph 77B7 compared to Morph 77b7 Δgas1

| Strain | Deletion | DO (%) | Agitation (rpm) | Biomass (g/kg) | CER (mmol/L/hr) |
|---|---|---|---|---|---|
| Morph 77b7 | none | 40 | 616 | 38 | 141 |
| Morph 77b7Δgas1 | gas1 | 115 | 500 | 39 | 147 |

E. Viscosity Reduction in Disrupted Crz1

In fungi, calcineurin mediated $Ca^{2+}$ signaling has been shown to be required for growth, development, and virulence in many organisms. It is necessary for adaption to diverse environmental conditions including high cation levels and alkaline pH. The gene crz1 encodes a calcineurin-regulated transcription factor. The Crz1p transcription factor is dephosphorylated when the phosphatase calcineurin is activated by $Ca^{2+}$/calmodulin. It then enters the nucleus and induces expression of a number of genes, many of which encode proteins with cell wall-related functions (Yoshimoto et al., 2002; Lagorce et al., 2003; Garcia et al., 2004; Karababa et al., 2006; Pardini et al., 2006, Munro, C. et al. 2009). Deletion of crz1 or a homolog can result in alterations in hyphal morphology (Kothe, G. and Free, S. 1998, Prokisch, H. et al. 1997).

A *Trichoderma reesei* Morph strain was prepared as described above. The *Trichoderma reesei* crz1 (PID 36391)

was deleted from mutant Morph 77B7. Strain Morph TrGA 77B7 Δpyr2 was transformed with the crz1 disruption cassette using PEG-mediated transformation, and plated on Vogel's minimal medium containing sorbitol to select for candidates based on uridine prototrophy acquired by the pyr2 marker. As shown in Table 6, Morph 77B7 Δcrz1 has a reduction in broth viscosity compared to the parent Morph 77B7. At the end of the batch growth phase, when all the glucose has been consumed, both strains had achieved a similar biomass concentration. To arrive at the end of the batch growth phase, the Morph 77B7 control strain saw agitation increased to 616 rpm and then saw DO content level drop down to as low as 40%. The strain Morph 77B7 Δcrz1 did not require as much energy to achieve the same biomass concentration. Agitation rate never increased above 500 rpm and the % DO never dropped below 100. Details of the crz1 disruption can be found in U.S. Provisional Application No. 61/480,610, filed Apr. 29, 2011, incorporated by reference herein in its entirety.

TABLE 6

Broth viscosity of Morph 77B7 compared to Morph 77b7 Δcrz1

| Strain | Deletion | DO (%) | Agitation (rpm) | Biomass (g/kg) | CER (mmol/L/hr) |
|---|---|---|---|---|---|
| Morph 77b7 | none | 40 | 616 | 38 | 141 |
| Morph 77b7Δcrz1 | crz1 | 100 | 500 | 39 | 120 |

Although the foregoing compositions and methods have been described in some detail by way of illustration and examples for purposes of clarity of understanding, it will be apparent to those skilled in the art that certain changes and modifications can be made. Therefore, the description should not be construed as limiting the scope of the invention, which is delineated by the appended claims.

All publications, patents, and patent applications cited herein are hereby incorporated by reference in their entireties for all purposes and to the same extent as if each individual publication, patent, or patent application were specifically and individually indicated to be so incorporated by reference.

REFERENCES

The following references, and additional reference cited herein, are hereby incorporated by reference:

Borgia, P. et al. (1996) *Mol. Microbiol.* 20:1287-1296.
Hughes, H. and Stephens, D. J. (2008) *Cell Biol.* 129:129-51.
Karhinen, L. et al. (2005) *Traffic* 6:562-74.
Passolunghi, S. et al. (2010) *Microbial Cell Factories* 9:7-17.
Peng, R. et al. (2000) *J. Biol. Chem.* 275:11521-28.
Roberg, K. J. et al. (1999) *J. Cell. Biol.* 145:659-72.
Shimoni, Y. et al. (2000) *J. Cell. Biol.* 151:973-84.
Simola, M et al. (2000) *Mol. Microbiol.* 37:42-53.
Singer, M. and Lindquist S. (1998) *Mol. Cell.* 5:639-48.
Turchini, A. et al. (2000) *J. Bacteriol.* 182:1167-71.

What is claimed is:

1. A variant strain of filamentous fungus derived from a parental strain, the variant strain comprising a genetic alteration that causes cells of the variant strain to produce a reduced amount of functional Tps2 protein compared to cells of the parental strain, wherein the Tps2 protein comprises 70% or greater sequence identity to a full length Tps2 protein of SEQ ID NO: 1, wherein the cells of the variant strain produce during aerobic fermentation in submerged culture a reduced viscosity cell broth compared to the cells of the parental strain.

2. The variant strain of claim 1, wherein the reduced viscosity cell broth (i) requires reduced agitation to maintain a preselected dissolved oxygen content compared to the cells of the parental strain, and/or (ii) maintains an increased dissolved oxygen content at a preselected amount of agitation compared to the cells of the parental strain.

3. The variant strain of claim 1, wherein the genetic alteration comprises a disruption of the tps2 gene present in the parental strain.

4. The variant strain of claim 3, wherein disruption of the tps2 gene is the result of deletion of all or part of the tps2 gene.

5. The variant strain of claim 3, wherein disruption of the tps2 gene is the result of deletion of a portion of genomic DNA comprising the tps2 gene.

6. The variant strain of any claim 3, wherein disruption of the tps2 gene is the result of mutagenesis of the tps2 gene.

7. The variant strain of claim 3, wherein disruption of the tps2 gene is performed using site-specific recombination.

8. The variant strain of claim 3, wherein disruption of the tps2 gene is performed in combination with introducing a selectable marker at the genetic locus of the tps2 gene.

9. The variant strain of claim 1, wherein the variant strain does not produce functional Tps2 protein.

10. The variant strain of claim 1, wherein the variant strain does not produce Tps2 protein.

11. The variant strain of claim 1, wherein the variant strain further comprises a gene encoding a protein of interest.

12. The variant strain of claim 1, further comprising a disruption of the sfb3 gene.

13. The variant strain of claim 1, further comprising a disruption of at least one gene selected from the group consisting of the sfb3 gene, the seb1 gene, the mpg1 gene, the gas1 gene, and the crz1 gene.

14. The variant strain of claim 1, wherein the variant strain produces substantially the same amount of, or more, protein per unit amount of biomass as the parental strain.

15. The variant strain of claim 1, wherein the filamentous fungus is a Pezizomycotina species.

16. The variant strain of claim 1, wherein the filamentous fungus is a *Trichoderma* spp.

17. The variant strain of claim 1, wherein the filamentous fungus is *Trichoderma reesei*.

18. A method for producing a variant strain of filamentous fungus cells comprising: introducing a genetic alteration into a parental strain of filamentous fungal cell, which genetic alteration reduces the production of functional Tps2 protein compared to the cells of the parental strain, wherein the Tps2 protein comprises 70% or greater sequence identity to the full length Tps2 protein of SEQ ID NO: 1, thereby producing a variant filamentous fungal cell that produces during aerobic fermentation in submerged culture a cell broth that (i) requires a reduced amount of agitation to maintain a preselected dissolved oxygen content, compared to the cells of the parental strain, and/or (ii) maintains an increased dissolved oxygen content at a preselected amount of agitation, compared to the cells of the parental strain.

19. The method of claim 18, wherein the genetic alteration prevents the production of functional Tps2 protein, thereby producing a variant filamentous fungal cell that produces during aerobic fermentation in submerged culture a cell broth that (i) requires reduced agitation to maintain a preselected dissolved oxygen content, compared to the cells of the parental strain, and/or (ii) maintains an increased dissolved oxygen content at a preselected amount of agitation, compared to the cells of the parental strain.

20. The method of claim 18, wherein the genetic alteration comprises disrupting the tps2 gene in a parental filamentous fungal cell using genetic manipulation.

21. The method of claim 18, wherein the genetic alteration comprises deleting the tps2 gene in a parental filamentous fungal cell using genetic manipulation.

22. The method of claim 18, wherein the genetic alteration is performed using site-specific genetic recombination.

23. The method of claim 18, wherein disruption of the tps2 gene is performed in combination with introducing a selectable marker at the genetic locus of the tps2 gene.

24. The method of claim 18, wherein disruption of the tps2 gene is performed in combination with disrupting the sfb3 gene.

25. The method of claim 18, wherein disruption of the tps2 gene is performed in combination with disruption of at least one gene selected from the group consisting of the sfb3 gene, the seb1 gene, the mpg1 gene, the gas1 gene, and the crz1 gene.

26. The method of claim 18, wherein the variant strain produces substantially the same amount of, or more, protein per unit amount of biomass as the parental strain.

27. The method of claim 18, wherein the filamentous fungus is a Pezizomycotina species.

28. The method of claim 18, wherein the filamentous fungus is a *Trichoderma* spp.

29. The method of claim 18, wherein the filamentous fungus is *Trichoderma reesei*.

30. The method of claim 18, wherein the parental strain further comprises a gene encoding a protein of interest.

31. The method of claim 30, wherein the gene encoding the protein of interest is present in the parental strain prior to introducing the genetic alteration that reduces or prevents the production of functional Tps2 protein.

32. A variant strain of filamentous fungus produced by the method of claim 18.

33. A variant strain of filamentous fungus derived from a parental strain, the variant strain comprising:
(a) a genetic alteration that causes cells of the variant strain to produce a reduced amount of functional Tps2 protein compared to cells of the parental strain, wherein the Tps2 protein comprises 70% or greater sequence identity to a full length Tps2 protein of SEQ ID NO: 1, wherein the cells of the variant strain produce during aerobic fermentation in submerged culture a reduced viscosity cell broth that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, and
(b) a gene encoding a protein of interest,
wherein the gene encoding the protein of interest is present in the variant strain prior to the genetic alteration in (a).

34. The variant strain of claim 33, wherein the genetic alteration comprises a disruption of the tps2 gene present in the parental strain.

35. The variant strain of claim 34, wherein disruption of the tps2 gene is performed in combination with introducing a selectable marker at the genetic locus of the tps2 gene.

36. The variant strain of claim 35, wherein disruption of the tps2 gene is performed in combination with disrupting at least one gene selected from the group consisting of the sfb3 gene, the seb1 gene, the mpg1 gene, the gas1 gene, and the crz1 gene.

37. The variant strain of claim 34, wherein disruption of the tps2 gene is performed in combination with disrupting the seb1 gene.

\* \* \* \* \*